(12) United States Patent
Diergaarde et al.

(10) Patent No.: US 9,856,486 B2
(45) Date of Patent: Jan. 2, 2018

(54) TRICHOME SPECIFIC PROMOTERS

(71) Applicant: Keygene N.V., Wageningen (NL)

(72) Inventors: Paul Johan Diergaarde, Wageningen (NL); Marinus Willem Prins, Wageningen (NL); Martin De Vos, Wageningen (NL)

(73) Assignee: Keygene N.V., Wageningen (NL)

(*) Notice: Subject to any disclaimer, the term of this patent is extended or adjusted under 35 U.S.C. 154(b) by 103 days.

(21) Appl. No.: 14/648,643

(22) PCT Filed: Nov. 29, 2013

(86) PCT No.: PCT/NL2013/050863
§ 371 (c)(1),
(2) Date: May 29, 2015

(87) PCT Pub. No.: WO2014/084739
PCT Pub. Date: Jun. 5, 2014

(65) Prior Publication Data
US 2015/0315602 A1 Nov. 5, 2015

Related U.S. Application Data

(60) Provisional application No. 61/731,739, filed on Nov. 30, 2012.

(30) Foreign Application Priority Data

Nov. 30, 2012 (NL) .................................. 2009915

(51) Int. Cl.
*C12N 15/82* (2006.01)

(52) U.S. Cl.
CPC .............................. *C12N 15/8223* (2013.01)

(58) Field of Classification Search
None
See application file for complete search history.

(56) References Cited

U.S. PATENT DOCUMENTS

2009/0253170 A1* 10/2009 Ronen .................. C07K 14/565
435/69.1
2010/0138954 A1 6/2010 Sallaud et al.

FOREIGN PATENT DOCUMENTS

WO WO-2004/111183 A2 12/2004
WO WO-2009/082208 A2 7/2009

OTHER PUBLICATIONS

Lieberman et al., Plant Physiol 33(5):307-11 (1958).*
Kyndt et al., Proc Natl Acad Sci 112(18):5844-49 (2015).*
Potenza et al., In Vitro Cell Dev Biol Plant 40:1-22 (2004).*
Saha et al., In Silico Biol 7(1):7-19 (2007).*
Wang et al., Mol Biol, 45(5):751-58 (2011).*
Ennajdaoui et al., Plant Mol Biol 73:673-85 (2010).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Falara et al., Plant Physiol 157(2):770-89 (2011).*
Vaughn et al., RNA 18:368-84 (2012).*
Xing & Li, WIREs RNA 2:445-58 (2011).*
USPTO Written Description Training Materials (2008).*
Aharoni, et al. "Metabolic engineering of terpenoid biosynthesis in plants", Phytochemistry Reviews, 2006, vol. 5, pp. 49-58.
B8XA40—ZFPS_SOLHA, UniProt (2Z,6Z)-farnesyl diphosphate synthase, chloroplastic (Mar. 3, 2009).
Bleeker, et al. "Improved herbivore resistance in cultivated tomato with the sesquiterpene biosynthetic pathway from a wild relative", PNAS (Dec. 4, 2012), vol. 109, No. 49, pp. 20124-20129.
Database EMBL (online) "Solanum lycopersicum germacrene synthase (TPS9) gene, complete cds", EBI Accession No. EM_STD:JN408289 (Aug. 15, 2011).
Falara, et al. "The Tomato Terpene Synthase Gene Family", Plant Pysiology (Oct. 2011), vol. 157, pp. 770-789.
International Search Report & Written Opinion in PCT/NL2013/050863 dated May 8, 2014.
Sallaud, et al. "A Novel Pathway for Sesquiterpene Biosynthesis from Z,Z-Farnesyl Pyrophosphate in the Wild Tomato *Solanum habrochaites*", The Plant Cell, Jan. 2009, vol. 21, pp. 301-317.
Search Report in NL Appln No. 2009915 dated Mar. 13, 2013.
Tissier, "Trichome Specific Expression: Promoters and Their Applications", In: "Transgenic Plants—Advances and Limitations", Intech(Mar. 7, 2012) pp. 353-378.
Notice of Reasons for Rejection issued in co-pending Japanese Application No. 2015-545413, dated Sep. 15, 2017.

* cited by examiner

*Primary Examiner* — Cathy Kingdon Worley
*Assistant Examiner* — Russell Boggs
(74) *Attorney, Agent, or Firm* — Foley & Lardner LLP

(57) ABSTRACT

Trichome specific plant promoters are provided herein. Also provided are transgenic cells and organisms, especially plant cell and plants, comprising such trichome-specific promoter or a chimeric or vector comprising such trichome-specific promoter. The invention further provides methods for expressing nucleic acid sequences in cells and organisms using trichome specific promoters.

13 Claims, 2 Drawing Sheets

TRICHOME SPECIFIC PROMOTERS

CROSS REFERENCE TO RELATED APPLICATIONS

The present application is a National Stage of International Application No. PCT/NL2013/050863 filed on Nov. 29, 2013, which was published on Jun. 5, 2014, as WO 2014/084739 A1, which claims the benefit of U.S. Application No. 61/731,739 filed Nov. 30, 2012 and NL Application No. 2009915 filed Nov. 30, 2012, the entire disclosures of which is incorporated herein by reference.

FIELD OF THE INVENTION

The present invention relates to trichome specific plant promoters and their uses. The promoters may be used for expression of homologous or heterologous proteins in trichome cells, or for the expression of active nucleic acid molecules, such as sense and/or anti-sense RNA. Provided are nucleic acid sequences having promoter activity, as well as chimeric genes, vectors and recombinant (transgenic) cells and organism comprising these. Also provided are methods for making transgenic cells and organisms, especially plants and plant cells, comprising the promoters. The promoters are useful for the production of various compounds in trichomes, such as pesticides, volatile oils, flavours or fragrances, pharmaceutical components, cytotoxic proteins and the like.

BACKGROUND OF THE INVENTION

Trichomes are various outgrowths of the epidermis in plants including branched and unbranched hairs, vesicles, hooks spines and stinging hairs. Trichomes are staked, multicellular protruding structures that are considered important in the protection of plants against herbivores, but also against water loss by transpiration and UV irradiation (Mauricio & Rausher, 1997, Evolution 51, 1435 Wagner et al. 2004, Ann Bot 93, 3), as sinks for toxic heavy metals and xenobiotics (Salt et al., 1995, Plant Phys 109, 1427; Domínguez-Solís et al. 2001, J Biol Chem 276, 9297; Gutiérrez-Alcalá et al. 2000, PNAS 97, 11108).

Glandular trichomes containing various secondary compounds are present on the foliage of many solanaceous species and their role in resistance to various pests has been well documented. Glandular trichomes in tomato contain high amounts of terpenes (van der Hoeven et al., Plant Cell. 2000, vol. 12(11):2283-2294) and methylketones (Fridman et al., Plant Cell 2005, vol. 17(4):1252-1267). Trichomes have been categorised into types I to VII (Luckwill, 1943, Aberdeen University Press, UK) with types I, IV, VI and VII as glandular trichome types and II, III, and V as non-glandular. Type IV, V and VI are the prevalent trichomes on the wild tomato S. habrochaites (Simmons and Gurr, 2005, Agricultural and Forest Entomol 7, 265). In S. pennelli resistance to pests is predominantly related to the chemistry and density of type IV glandular trichomes, which cover all parts of the plant (Simmons et al., 2003 Aus J Entomol 43, 196; 2004, Entomol Exp App 113, 95). When exudates of glandular trichomes are physically removed, pest survival and longevity increases while mortality and entrapment decreases (Simmons and Gurr, 2005, Agricultural and Forest Entomol 7, 265). Trichome types IV and VI have been positively correlated with pest control.

Non-glandular trichomes of cotton ovules have been explored as targets for biotechnology with high economic importance (Kim and Triplett, 2001, Plant Physiol 127, 1361). The ability of glandular trichomes to secrete various phytochemicals, such as acyl sugars in S. pennelli and methyl ketones and terpenes in S. habrochaites, makes these structures potentially suitable for biotechnological application and provides opportunities for trichome based pest management.

Protein expression in trichomes can be utilised for the production of useful compounds such as pesticides, pharmaceutical components, volatile oils, flavours and fragrances (Callow, 2000 Advances in botanical research eds. Hallahan and Gray, San Diego Academic Press; Wagner 2004 Ann Bot 93, 3). In order to generate components specifically in trichomes, regulation of gene expression in the plant trichome is necessary. The possibility to direct protein expression in specialised structures or cells avoids interference in the plant metabolic pathways and consequently the performance of the plant.

Constitutive strong promoters such as the well known Cauliflower Mosaic Virus promoter (CaMV 35S) promoter are generally used in ectopic-expression studies. However this type of promoter is not very suitable for the expression of specific and possibly phytotoxic compounds, such as terpenes. Moreover, exhaustion of metabolic pools might be problematic.

Gutierrez-Alcala (2005, J Exp Bot 56, 2487) describes the promoter of the *Arabidopsis thaliana* OASA1 gene, which has activity in both glandular and non-glandular trichomes of tobacco.

Wang et al. (2002, J Exp Bot 53, 1891) describes a trichome specific promoter from tobacco P450 gene, CYP71D16, which shows expression in tobacco glandular trichomes at all developmental stages.

WO2004/111183 describes trichome specific promoters from tomato and tobacco leaves. However, upon testing transgenics described in WO2004/111183 no satisfactory results were obtained in the sense that expression was not trichome specific (e.g. additional expression in leaf veins) and expression was weak.

WO2009/082208 describes trichome-specific promoters from tomato. Although these promoters have been shown to be strictly trichome-specific, their activity is relatively low.

Despite trichome specific promoters having been isolated, none show a combination of trichome-specificity and high promoter activity. There is a clear need for highly active trichome-specific or trichome preferred promoters. Moreover, ideally several such promoters should be identified in order to successfully engineer the production of useful compounds in trichomes. Biosynthesis of these compounds often require the use of multiple genes, and thus ideally these multiple genes are expressed in trichomes, preferably using various promoters.

Such new plant promoters should ideally have the following requirements: i. organ/tissue specificity, the promoters should be strictly trichome-specific to avoid potentially unwanted compound production in other tissues (e.g. edible part); ii. high promoter activity.

The present invention provides trichome specific transcription regulatory sequences which are suitable for directing expression of operably linked nucleic acid molecules in glandular and non-glandular trichomes, especially in glandular trichomes found on various plant surfaces (aerial parts such as leaves, stems, floral organs) while, in some species, they are absent from particular plant surfaces such as the fruit and seeds. Simple trichomes are present on aerial surfaces of most angiosperms and some gymnosperms and bryophytes (Wagner et al. 2004, Ann Bot 93, 3). In angiosperms trichomes may occur on leaves, petals, petioles, peduncles, stems and seed coats, depending on the species. Glandular trichomes are found on perhaps 30% of vascular plants (Dell and McComb, 1978, Adv Bot Res 6, 227; Fahn, 2000 Adv Bot Res 31, 37).

SUMMARY OF THE INVENTION

Provided are nucleic acid sequences, fragments of nucleic acid sequences, uses and applications of the promoters of ShzFPS, ShZIS and ShTPS9.

Provided is a transgenic plant or plant cell or plant tissue or organ comprising a chimeric gene integrated in its genome, characterized in that said chimeric gene comprises a trichome specific promoter operably linked to a homologous or heterologous nucleic acid sequence, wherein the promoter is selected from the group of:
  (a) the nucleic acid sequence of SEQ ID NO: 4 SEQ ID NO: 3, SEQ ID NO:1 or SEQ ID NO: 2 (or its complement),
  (b) a functional fragment of the nucleic acid sequence of SEQ ID NO: 4, SEQ ID NO: 3, SEQ ID NO:1 or SEQ ID NO: 2 (or its complement);
  (c) a nucleic acid sequence comprising at least 70% sequence identity with the nucleic acid sequence of SEQ ID NO: 4, SEQ ID NO: 3, SEQ ID NO:1 or SEQ ID NO: 2 (or its complement);
  (d) a functional fragment of the nucleic acid sequence of (c) comprising transcription regulatory activity.

Also provided is an isolated nucleic acid sequence having promoter activity when introduced into plant cells, wherein said nucleic acid sequence comprising a sequence selected from:
  (a) the nucleic acid sequence of SEQ ID NO: 4, SEQ ID NO: 3, SEQ ID NO:1 or SEQ ID NO: 2 (or its complement),
  (b) a functional fragment of the nucleic acid sequence of SEQ ID NO: 4, SEQ ID NO: 3, SEQ ID NO:1 or SEQ ID NO: 2 (or its complement);
  (c) a nucleic acid sequence comprising at least 70% sequence identity with the nucleic acid sequence of SEQ ID NO: 4, SEQ ID NO: 3, SEQ ID NO:1 or SEQ ID NO: 2 (or its complement);
  (d) a functional fragment of the nucleic acid sequence of (c) comprising transcription regulatory activity.

Vectors, chimeric genes and host cells comprising the above sequences are also an embodiment of the invention.

Further, a method is provided for making a transgenic plant or plant cell, comprising the steps of:
  (a) generating a chimeric gene comprising a promoter as described above, operably linked to a nucleic acid sequence to be transcribed, and optionally further linked to a 3'UTR nucleic acid sequence, or a vector comprising the promoter as described above or a chimeric gene as described above;
  (b) transforming a plant or plant cell with said chimeric gene or vector; and, optionally.
  (c) regenerating transgenic plants or plant cells.

The method may further comprise growing the transgenic plant (or a derivative thereof, such as derived from crossing or selfing and wherein the derivative retains the chimeric gene) and harvesting the trichomes or parts thereof (trichome exudates) for further use (molecular farming).

Alternatively, for example if the chimeric gene increases pest and/or pathogen resistance of the plant, the method may further comprise growing the transgenic plant (or a derivative thereof, such as derived from crossing or selfing and wherein the derivative retains the chimeric gene) and harvesting all or part of the plant, such as the leaves, fruit, seeds, etc. for further use.

The promoter sequences provided here exhibit a high activity and trichome specific, preferably glandular trichome-specific, expression. In contrast to earlier reported trichome-specific promoters, the promoter sequences provided herein are highly trichome-specific and result in high expression of the genes they drive. Additionally, it is shown here that the promoter sequence from a wild tomato is active in the trichomes of a cultivated tomato and other trichome-bearing plant species.

Finally, provided are uses and applications of the sequences or fragments of nucleic acid sequences of the promoters of ShzFPS and ShZIS in combination with their respective coding sequences for providing plants, plant cells or plant organs that show high expression of zFPS and ZIS in trichomes, preferably glandular trichomes, and high levels of accumulation in trichomes of 7-epizingiberene or terpenoids alike.

GENERAL DEFINITIONS

"Trichome" encompasses herein different types of trichomes, both glandular trichomes and/or non-glandular trichomes.

"Trichome cells" refers to the cells making up the trichome structure, such as the gland, or secretory cells, base cells and stalk, or stipe cells, extra-cellular cavity and cuticle cells. Trichomes can also consist of one single cell.

"Molecular farming" refers herein to the production and/or recovery of useful compounds from trichomes of transgenic plants expressing one or more chimeric genes in trichomes, whereby for example secondary metabolites, pharmaceutical compounds, fragrances or flavours are produced in the trichomes.

The term "nucleic acid sequence" (or nucleic acid molecule) refers to a DNA or RNA molecule in single or double stranded form, particularly a DNA having promoter activity according to the invention or a DNA encoding a protein or protein fragment. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA) in a cell, operably linked to suitable transcription regulatory regions (e.g. a promoter). A gene may thus comprise several operably linked sequences, such as a promoter, a 5' non-translated leader sequence (also referred to as 5'UTR, which corresponds to the transcribed mRNA sequence upstream of the translation start codon) comprising e.g. sequences involved in translation initiation, a (protein) coding region (cDNA or genomic DNA) and a 3' non-translated sequence (also referred to as 3' untranslated region, or 3'UTR) comprising e.g. transcription termination sites and polyadenylation site (such as e.g. AAUAAA or variants thereof).

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more sense sequences (e.g. coding sequences) or to an antisense (reverse complement of the sense strand) or inverted repeat sequence (sense and antisense, whereby the RNA transcript forms double stranded RNA upon transcription).

A "3' UTR" or "3' non-translated sequence" (also often referred to as 3' untranslated region, or 3' end) refers to the nucleic acid sequence found downstream of the coding sequence of a gene, which comprises, for example, a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

"Expression of a gene" refers to the process wherein a DNA region, which is operably linked to appropriate regulatory regions, particularly a promoter, is transcribed into a RNA, which is biologically active, i.e. which is capable of being translated into a biologically active protein or peptide (or active peptide fragment) or which is active itself (e.g. in posttranscriptional gene silencing or RNAi, or silencing through miRNAs). An active protein in certain embodiments refers to a protein having a dominant-negative function due to a repressor domain being present. The coding sequence is preferably in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation. Down-regulation of gene expression can also take place through the action of microRNAs (miRNA), endogenous 21-24 nucleotide small RNAs processed from stem-loop RNA precursors (pre-miRNAs), Incorporated into a RNA-induced silencing complex (RISC), miRNAs down-regulate gene expression by mRNA cleavage or translational repression.

"Ectopic expression" refers to expression in a tissue in which the gene is normally not expressed.

A "transcription regulatory sequence" is herein defined as a nucleic acid sequence that is capable of regulating the rate of transcription of a nucleic acid sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers, but also silencers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream (5') with respect to the direction of transcription of the transcription initiation site of the gene (the transcription start is referred to as position +1 of the sequence and any upstream nucleotides relative thereto are referred to using negative numbers), and is structurally identified by the presence of a binding site for DNA-dependent RNA polymerase, transcription initiation sites and any other DNA domains (cis acting sequences), including, but not limited to transcription factor binding sites, repressor and activator protein binding sites, and any other sequences of nucleotides known to one of skill in the art to act directly or indirectly to regulate the amount of transcription from the promoter. Examples of eukaryotic cis acting sequences upstream of the transcription start (+1) include the TATA box (commonly at approximately position −20 to −30 of the transcription start), the CAAT box (commonly at approximately position −75 relative to the transcription start), 5' enhancer or silencer elements, etc.

A "constitutive" promoter (such as the CaMV 35S promoter) is a promoter that is active in essentially all tissues and organs under most physiological and/or developmental conditions. More preferably, a constitutive promoter is active under essentially all physiological and developmental conditions in all major organs, such as at least the leaves, stems, roots, seeds, fruits and flowers. Most preferably, the promoter is active in all organs under most (preferably all) physiological and developmental conditions.

However, a tissue-specific or tissue-preferred promoter (such as the promoters according to the invention) can also be referred to as being "constitutively active". The promoter is thus active under most developmental and/or physiological conditions, albeit in only a specific tissue or mainly in a specific tissue. A "promoter which has constitutive activity" or which is "constitutive" in a plant or plant cell refers, therefore, to a nucleic acid sequence which confers transcription in the plant or plant cells in the specific tissue under most physiological and developmental conditions.

An "inducible" promoter is a promoter that is physiologically (e.g. by external application of certain compounds) or developmentally regulated.

A "tissue specific" promoter is only active in specific types of tissues or cells, such as trichome cells. The promoter activity can therefore be described by referring to the circumstances under which the promoter confers transcription of the nucleic acid sequence operably linked downstream (3') of the promoter.

A "tissue preferred" promoter is preferentially, but not exclusively, active in certain tissues or cells, such as for example in trichome cells and epidermis cells.

A promoter which is "insensitive to one or more biotic and/or abiotic stresses" or whose activity "is not reduced when exposed to one or more biotic and/or abiotic stress conditions" refers to a nucleic acid sequence having promoter activity under normal physiological and developmental conditions, and whereby the activity is not, or at least not significantly, reduced quantitatively when biotic and/or abiotic stress is exerted on the organism (e.g. plant) or cells or tissues or organs comprising the promoter.

"Stress" refers to conditions or pressures of physical, chemical or biological origin acting on a plant or plant cells which may result in yield loss and/or quality loss of a plant, but which is not lethal to the plant. "Non-stress conditions" refer herein to conditions under which physiology and development are normal or optimal. "Biotic stress" refers to stress caused by biotic (live) agents, such as fungi, viruses, mycoplasma like organisms, insects, arthropods, bacteria, nematodes etc. (i.e. especially plant pests and pathogens). "Abiotic stress" refers to stress caused by abiotic (non-living) agents, such as temperature stress (cold/freezing, heat), salinity (salt), wind, metals, day-length (photoperiod), water-stress (such as too little or too much water availability, i.e. drought, dehydration, water-logging, etc.), etc.

As used herein, the term "operably linked" refers to a linkage of polynucleotide elements in a functional relationship. A nucleic acid is "operably linked" when it is placed into a functional relationship with another nucleic acid sequence. For instance, a promoter, or a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which are joined to form a functional protein, which displays the functionality of the joined domains (for example a DNA binding domain or a repression of function domain leading to a dominant negative function). A chimeric protein may also be a fusion protein of two or more proteins occurring in nature. The term "domain" as used herein means any part(s) or domain(s) of the protein with a specific structure or function that can be transferred to another protein for providing a new hybrid protein with at least the functional characteristic of the domain.

The term "target peptide" refers to amino acid sequences which target a protein to intracellular organelles such as plastids, preferably chloroplasts, mitochondria, or to the extracellular space (secretion signal peptide). A nucleic acid sequence encoding a target peptide may be fused (in frame) to the nucleic acid sequence encoding the amino terminal end (N-terminal end) of the protein. For example, target peptides for trichome cells include peptides which target leucoplasts, chloroplasts, mitochondria, nuclei, peroxisomes, endoplasmatic reticulum, plastids, extra-cellular cavities or vacuoles of the trichome cells.

A "nucleic acid construct" or "vector" is herein understood to mean a man-made nucleic acid molecule resulting from the use of recombinant DNA technology and which is used to deliver exogenous DNA into a host cell. The vector backbone may for example be a binary or superbinary vector (see e.g. U.S. Pat. No. 5,591,616, US2002138879 and WO 95/06722), a co-integrate vector or a T-DNA vector, as known in the art and as described elsewhere herein, into which a chimeric gene is integrated or, if a suitable transcription regulatory sequence/promoter is already present, only a desired nucleic acid sequence (e.g. a coding sequence, an antisense or an inverted repeat sequence) is integrated downstream of the transcription regulatory sequence/promoter. Vectors usually comprise further genetic elements to facilitate their use in molecular cloning, such as e.g. selectable markers, multiple cloning sites and the like (see below).

A "host cell" or a "recombinant host cell" or "transformed cell" are terms referring to a new individual cell (or organism), arising as a result of the introduction into said cell of at least one nucleic acid molecule, especially comprising a chimeric gene encoding a desired protein or a nucleic acid sequence which upon transcription yields an antisense RNA or an inverted repeat RNA (or hairpin RNA) for silencing of a target gene/gene family. The host cell is preferably a plant cell, but may also be a bacterial cell, a fungal cell (including a yeast cell), etc. The host cell may contain the nucleic acid construct as an extra-chromosomally (episomal) replicating molecule, or more preferably, comprises the chimeric gene integrated in the nuclear or plastid genome of the host cell.

The term "selectable marker" is a term familiar to one of ordinary skill in the art and is used herein to describe any genetic entity which, when expressed, can be used to select for a cell or cells containing the selectable marker. Selectable marker gene products confer, for example, antibiotic resistance, or more preferably, herbicide resistance or another selectable trait such as a phenotypic trait (e.g. a change in pigmentation) or a nutritional requirement. The term "reporter" is mainly used to refer to visible markers, such as green fluorescent protein (GFP), eGFP, luciferase, GUS and the like, as well as nptII markers and the like.

The term "ortholog" of a gene or protein refers herein to the homologous gene or protein found in another species, which has the same function as the gene or protein, but (usually) diverged in sequence from the time point on when the species harbouring the genes diverged (i.e. the genes evolved from a common ancestor by speciation). Orthologs of a gene from one plant species may thus be identified in other plant species based on both sequence comparisons (e.g. based on percentages sequence identity over the entire sequence or over specific domains) and functional analysis.

The terms "homologous" and "heterologous" refer to the relationship between a nucleic acid or amino acid sequence and its host cell or organism, especially in the context of transgenic organisms. A homologous sequence is thus naturally found in the host species (e.g. a tomato plant transformed with a tomato gene), while a heterologous sequence is not naturally found in the host cell (e.g. a tomato plant transformed with a sequence from potato plants). Depending on the context, the term "homolog" or "homologous" may alternatively refer to sequences which are descendent from a common ancestral sequence (e.g. they may be orthologs).

"Stringent hybridisation conditions" can be used to identify nucleotide sequences, which are substantially identical to a given nucleotide sequence. The stringency of the hybridization conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt (NaCl) concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"High stringency" conditions can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency" refers to conditions equivalent to hybridization in the above described solution but at about 60-62° C. In that case the final wash is performed at the hybridization temperature in 1×SSC, 0.1% SDS.

"Low stringency" refers to conditions equivalent to hybridization in the above described solution at about 50-52° C. In that case, the final wash is performed at the hybridization temperature in 2×SSC, 0.1% SDS. See also Sambrook et al. (1989) and Sambrook and Russell (2001).

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as using the Smith Waterman algorithm, are preferred. Alternatively percentage similarity or identity may be determined by searching against public databases, using algorithms such as FASTA, BLAST, etc.

The abbreviation "Sh" preceding a gene name indicates that the gene is derived from *Solanum habrochaites*, whereas the abbreviation "Sl" preceding a gene name denotes that the gene is derived from *Solanum lycopersicum*. The abbreviation "FPS" refers to farnesyl pyrophosphate synthase, the abbreviation "ZIS" refers to zingiberene synthase, and the abbreviation "TPS9" refers to terpene synthase 9, which is a germacrene synthase. The abbreviation "zFPS" refers to a Z,Z-farnesyl pyrophosphate synthase (also referred to as "Z,Z-farnesyl diphosphate synthase").

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

Whenever reference to a "plant" or "plants" (or a plurality of plants) according to the invention is made, it is understood that also plant parts (cells, tissues or organs, seeds, severed or harvested parts, leaves, seedlings, flowers, pollen, fruit, stems, roots, callus, protoplasts, etc), progeny or clonal propagations of the plants which retain the distinguishing characteristics of the parents (e.g. presence of a trans-gene), such as seed obtained by selfing or crossing, e.g. hybrid seed (obtained by crossing two inbred parental lines), hybrid plants and plant parts derived therefrom are encompassed herein, unless otherwise indicated.

DETAILED DESCRIPTION

A constitutive promoter such as CaMV 35S promoter (single 35S promoter, described by Franck et al., 1980, Cell 21, 285-294) is not considered useful for the expression of genes which need to be regulated at a specific tissue level, e.g., in phloem or in trichomes, or under specific conditions only, e.g. stress-induced conditions.

In the present invention several plant promoters are provided which exhibit a constitutively high but tissue specific activity in trichomes, and are optionally essentially insensitive to one or more biotic and/or abiotic stresses. Such promoters are desired for the controlled expression of nucleic acid sequences in transgenic plants.

In one embodiment the invention provides promoter regions of tomato genes (tomato terpene synthases and orthologs and homologs thereof) which confer high, trichome specific, preferably glandular trichome-specific, expression in host plants, such as cultivated tomato (*Solanum lycopersicum*), other Solanaceae and other plant families and species.

Nucleic Acid Sequences, Chimeric Genes and Vectors

In one embodiment isolated nucleic acid sequences (preferably genomic or synthetic DNA sequences), having promoter activity in plant cells, are provided which show strong, high, preferably constitutive, transcriptional trichome specific activity in plant trichomes, such as in trichomes found on leaves, stems and flower organs. Preferably, the promoters are active in one or more glandular trichomes (types I, IV, VI and/or VII).

Preferably the promoter activity of the nucleic acid sequences according to the invention is not reduced, or at least not significantly reduced, when the transgenic plant, or plant tissue or organ, is subjected to one or more abiotic and/or biotic stresses. A significant reduction in this respect refers to a statistically significant (quantitative) reduction of promoter activity by 1% or more (e.g. 2%, 3%, 5%, 10%, etc., up to 100%) compared to the activity in the same tissues or organs under non-stress conditions. Thus, preferably the promoters remain strong and constitutive (in trichome cells) under one or more stress conditions.

In one embodiment a trichome specific promoter is provided comprising or consisting of SEQ ID NO: 4, SEQ ID NO: 3, SEQ ID NO:1 or SEQ ID NO: 2, or a nucleotide sequence essentially similar thereto (referred to as "variants", see definition below), or active (functional) fragments of any of these which have promoter activity in one or more trichome types and/or trichome cells, such as fragments of at least 200, 300, 400, 500, 600, 800, 900, 1000, 1200, 1500, 2000, 2400 or more consecutive nucleotides of SEQ ID NO: 4, 3, 1 or 2, or of variants thereof.

"Active fragments" or "functional fragments", or "fragments having promoter activity" refer to nucleic acid fragments which are capable of conferring transcription in one or more trichome types and/or one or more trichome cells found on one or more different types of plant tissues and organs (e.g. on stems, leaves, flower buds or flower parts). Preferably active fragments confer trichome specific and/or at least trichome preferred expression, and they preferably have at least a similar strength (or higher strength) as the promoter of SEQ ID NO: 4, 3, 1 or 2. This can be tested as described below, by transforming a plant with such a fragment, preferably operably linked to a reporter gene, and assaying the promoter activity qualitatively (spatio-temporal transcription) and/or preferably quantitatively in trichomes. Obviously, DNA fragments may be generated in a number of ways, e.g. using de novo DNA synthesis, or restriction enzymes, or terminal nucleases, etc. Deletion analysis, whereby fragments are generated which comprise 5' deletions of various sizes can for example be used to create stronger and/or more specific transcriptional activity.

In one embodiment, the strength of the promoter and/or promoter fragments is quantitatively essentially identical to, or higher than, that of the 35S promoter when measured in the glandular trichome. Preferably, the strength of the promoter and/or promoter fragments is quantitatively also essentially identical to, or higher than, that of the *Solanum lycopersicum* methylketone synthase 1 (MKS1) promoter (promoter of MKS1; Sol Genomics Network entry Solyc01g108780.2) when measured in the glandular trichome.

The promoters comprising or consisting of SEQ ID NO: 4, 3, 1 or 2, variants thereof or functional fragments of any of these, are preferably insensitive to at least one (but preferably more, most preferably any) biotic and/or abiotic stress/es to which the plant or plant cell(s), tissues or organs comprising the promoter may be exposed (see below). Thus, activity remains constitutive and strong in the trichomes during exposure to one or more stress conditions.

Also provided are "variants" of the above trichome specific promoters, and functional fragments of such variants. These variants include nucleic acid sequences essentially similar to SEQ ID NO: 4 and/or SEQ ID NO: 3 and/or SEQ ID NO: 1 and/or SEQ ID NO:2 (and functional fragments of these variant sequences, as described above), and which have promoter activity, i.e. which are also capable of providing (preferably constitutive, more preferably constitutively high) transcription in plant trichomes. Sequences which are "essentially similar" to SEQ ID NO: 4 and/or 3 and/or 1 and/or SEQ ID NO:2 are nucleic acid sequences comprising at least about 50, 55, 60, 65, 70, 75, 80, 85, 90, 95, 96, 97, 98, 99% or more nucleic acid sequence identity to SEQ ID NO: 4 and/or to SEQ ID NO: 3 and/or SEQ ID NO: 1 and/or SEQ ID NO:2, using the Needleman and Wunsch or the Smith Waterman Pairwise alignment (e.g. program "needle" or "water" in Embosswin, e.g. version 2.10.0, with default gap creation and gap extension penalties) and which are trichome specific in their activity. In a preferred embodiment, the activity of the variants (and functional fragments) is strong in trichomes, i.e. quantitatively at least as strong (or stronger) than the activity provided by SEQ ID NO: 4, 3, 2 or 1. Also the cell type specificity is at least as the specificity of SEQ ID NO: 4, 3, 2 or 1 or more specific. In a further embodiment the activity of these variants (and functional fragments thereof) is insensitive to one or more biotic and/or abiotic stresses.

It is clear that many methods can be used to identify, synthesise or isolate variants or functional fragments of the nucleic acid sequences provided herein, such as nucleic acid hybridization, PCR technology, in silico analysis and nucleic acid synthesis, and the like. For example, nucleic acid hybridization can be used to identify DNA sequences in other plant species or varieties which hybridize to SEQ ID NO: 4, 3, 1 or 2, or to fragments of these, under stringent or moderately stringent hybridization conditions.

Alternatively, sequence databases can be screened in silico for variant sequences using known algorithms, such as BLAST, FASTA, etc. In this way it is feasible to isolate variant sequences from other plant species or other varieties of tomato. Especially included herein are the promoters of other alleles of the same genes (ShzFPS, ShZIS and ShTPS9) found in other varieties of tomato or in other plant species, especially species of the genus *Solanum*, as will be described below. For example, cDNA libraries may be constructed from one or more plant species, one or more varieties, or different tissues of one species or variety. The cDNA libraries may be screened for monoterpene synthase 1 or sesquiterpene synthase 1 cDNAs (using e.g. probes or primers derived from SEQ ID NO: 4, 3, 1, 2, or fragments or variants thereof). Equally, differential display methods (such as cDNA-AFLP) may be used to identify such transcripts. Methods such as TAIL-PCR (Liu et al. 1995, Genomics 25(3):674-81; Liu et al. 2005, Methods Mol Biol. 286:341-8), Linker-PCR, or Inverse PCR (IPCR) may be used to isolate the upstream transcription regulatory region of the gene.

Variants of the same genes, i.e. orthologs and/or homologs of the genes encoding farnesyl diphosphate synthase (ShzFPS), zingiberene synthase (ShZIS) and germacrene synthase (ShTPS9), respectively, include for example nucleic acid sequences (DNA or RNA) or amino acid sequences comprising at least 50, 55, 60, 65, 70, 75, 80, 85, 90, 95, 96, 97, 98, 99% or more nucleic acid or amino acid sequence identity to the nucleotide sequence or amino acid sequence of GenBank Accession numbers FJ194969 (*S. habrochaites* zFPS cDNA and protein; Sallaud et al., 2009—Plant Cell), JN990661 (*S. habrochaites* ZIS; Gonzalers-Vigil et al., 2012—Plant Journal cDNA and protein), and JN402388 (*S. habrochaites* TPS9 cDNA; Bleeker et al. 2011—Plant Mol. Biol. 77(4-5):323-336). Preferably sequence identity is determined by pairwise alignment using the Needleman and Wunsch or the Smith Waterman Pairwise alignment (e.g. program "needle" or "water" in Embosswin, e.g. version 2.10.0, with default gap creation and gap extension penalties). The promoters of these variants are preferably also trichome specific in their activity. Methods such as cDNA-AFLP, other PCR based methods or Northern hybridization may be used to isolate or identify such genes. Their promoter can be cloned using known methods. In a preferred embodiment, the promoter is obtained from a ShzFPS ShZIS, or ShTPS9 gene from a plant belonging to the family Solanaceae, such as species of the genus *Solanum* (including the reclassified *Lycopersicon* species), *Nicotiana, Capsicum, Petunia, Coffea*, etc. Especially orthologs from wild species are desired.

Whether a nucleic acid sequence (or fragment of variant) has constitutive promoter activity, i.e. is capable of conferring transcription specifically in trichomes, whether the activity is "strong", and whether the activity of the nucleic acid sequence is insensitive to at least one (but preferably more, most preferably any) biotic and/or abiotic stress to which the transgenic cell, tissue, organ or organisms (especially plant or plant cell), may be exposed, can be determined using various methods. Generally, one can distinguish qualitative methods and quantitative methods. Qualitative methods (such as histological GUS staining) are used to determine the spatio-temporal activity of the promoter (is the promoter active or not in a certain tissue or organ, or under certain environmental; developmental conditions), while quantitative methods (such as fluorometric GUS assays) also quantify the level of activity, compared to controls. Suitable controls are, for example, plants transformed with empty vectors (negative control) or transformed with constructs comprising other promoters, such as the *Arabidopsis* CER6 promoter (Hooker et al. 2002, Plant Phys 129, 1568) which is active in the epidermis and trichomes of *N. tabacum*, or non-transgenic *Arabidopsis* plants.

To test and optionally quantify the relative or absolute activity, a cloned or synthetic nucleic acid molecule, such as SEQ ID NO: 4, 3, 1 or 2, or variants thereof, or fragments of any of these, may be operably linked to a known nucleic acid sequence (e.g. a reporter gene, such as gusA, or any gene encoding a specific protein) and may be used to transform a plant cell using known methods and regenerate a plant therefrom.

The activity of the promoter can, for example, be assayed (and optionally quantified) by detecting the level of RNA transcripts of the downstream nucleic acid sequence, especially in the trichome cells. This may be done using quantitative methods, such as e.g. quantitative RT-PCR or other PCR based methods, and the like. Alternatively, the reporter protein or the activity of the reporter protein may be assayed and quantified. For example, if the reporter gene is the gus gene, a fluorometric GUS assay may be used, as described in the Examples. In this way, the quantitative promoter activity levels of transformed plants or plant cells maintained under normal physiological (non-stress) conditions can be compared to levels of plants or plant cells which are exposed to one or more biotic or abiotic stresses. Also, relative or absolute activity levels in the trichome cells can be compared to constitutive control promoters, such as the 35S promoter, double-35S promoter, or to other promoters which have activity in trichomes, such as the MKS1 promoter, CYP71D16 promoter or OASA1 promoter. It is understood that preferably average promoter activity levels are determined and compared using statistical methods.

Thus, whether activity is found in trichome cells at a certain time (spatio-temporal activity) can, for example, be tested by transforming plants or plant cells with a promoter-reporter gene construct and analyzing trichomes during various developmental stages for the RNA transcript or reporter protein (or its activity). One simple test employs for example histochemical GUS staining, whereby visual assessment of blue colour indicates activity in trichomes and at various developmental stages of the trichomes.

As already mentioned, it is preferred that the promoter activity is constitutive and preferably also strong in trichome cells, especially in the host species or variety into which the sequence is introduced. Constitutive activity means that the transcript of any nucleic acid sequence operably linked to the promoter is preferably produced in trichome cells under most (normal, non-stressed) physiological and developmental conditions. In one embodiment, the promoters according to the invention are preferably not active in epidermal cells. Preferably the promoters are active in all glandular trichomes found on stems, flowers and/or (young) leaves. Preferably, the promoters according to the invention provide strong, constitutive activity in trichomes of all plant species, both dicotyledonous species and monocotyledonous species, such as described below (e.g. tomato, tobacco, *Brassica*, melon and lettuce and others).

The strength (quantitative activity) of the promoters according to the invention (including fragments or variants) in terms of its ability to drive expression of nucleic acid sequences linked downstream (3') can be determined quantitatively using various known methods. For example, the amount of transcribed transcript (mRNA) can be quantified using northern blotting or quantitative RT-PCR or next generation sequencing. Preferably, the promoter strength is at least essentially equal to the activity in the trichomes of the CaMV 35S (Franck et al., supra) under normal (non-stressed) conditions. "Strong" means, thus, that the promoter strength is preferably at least about identical, but more preferably stronger than that of the 35S promoter in trichomes under normal, non-stressed conditions. Most preferably, the average quantitative promoter activity in the trichomes is at least equivalent to the activity of the CaMV 35S promoter, or is at least 5%, 10%, 20%, 30%, 35%, 40%, 45%, 50%, 55%, 60%, 70%, 75%, or more, higher than the average activity of the CaMV 35S promoter in trichomes. It is understood that the same copy number and zygosity level of transformants should be compared, e.g. hemizygous or homozygous for the transgene. Preferably, single copy transformants are identified and compared. The strength of the 35S promoter in the trichomes of a host plant can be tested by analyzing and preferably quantifying e.g. GUS gene expression in a p35S-GUS plant and comparing this to the expression of the promoters according to the invention.

Preferably, the promoter strength is at least essentially equal to the activity in trichomes of the *Solanum lycopersicum* methylketone synthase 1 (SlMKS1) promoter (Fridman et al., supra) under physiological (non-stressed) conditions. "Strong" means, thus, that the promoter strength is preferably at least about identical, but more preferably stronger than that of the SlMKS1 promoter in trichomes under physiological, non-stressed conditions. Most preferably, the average quantitative promoter activity in the trichomes is at least equivalent to the activity of the SlMKS1 promoter, or is at least two-fold, 4-fold, 6-fold, 8-fold, 10-fold or more, higher than the average activity of the SlMKS1 promoter in trichomes. It is understood that the same copy number and zygosity level of transformants should be compared, e.g. hemizygous or homozygous for the transgene. Preferably, single copy transformants are identified and compared. The strength of the SlMKS1 promoter in the trichomes of a host plant can be tested by analysing and preferably quantifying e.g. GUS gene expression in a p SlMKS1-GUS plant and comparing this to the expression of the promoters according to the invention.

Thus, the strength of the promoters according to the invention preferably remains essentially unchanged, or is at least not reduced (or not significantly reduced), when the plant tissues or organs or plants comprising the promoter are exposed to stress conditions, selected at least from one or preferably several of: drought stress, heat stress, water-stress (both too much and too little water), pathogen stress (e.g. virus infection such as CMV, fungal infection, bacterial infection, etc.), pest stress (e.g. insect feeding), wounding, salt stress, radiation stress, etc. Again, quantitative tests can be used to determine this. For example, recombinant plants comprising the promoter may be transferred from a normal temperature environment to a warm environment (such as about 27° C. to up to about 50° C.), and the promoter activity in various tissues may be compared to the activity in the same tissues under the normal and under the warm temperature conditions.

In one embodiment the use of any of the above promoters for the expression of homologous or heterologous nucleic acid sequences in a recombinant cell or organism, especially a plant cell or plant, is provided. This use comprises operably linking the promoter to a homologous or heterologous nucleic acid sequence and transforming a plant or plant cell, as described further below.

Although the focus above is on the use of the promoters according to the invention in plants and plant cells, it is also an embodiment of the invention to use the promoters for the expression of homologous or heterologous nucleic acid sequences in other cells and organisms, such as in any prokaryotic or eukaryotic cells or organisms, e.g. bacteria, fungi (including yeasts, such as *Pichia, Hansenula*, etc.), mammals, human cells or cell lines, etc.

Chimeric Genes and Vectors According to the Invention

In one embodiment of the invention any of the above nucleic acid sequences having promoter activity, are used to make chimeric genes, and vectors comprising these for transfer of the chimeric gene into a host cell and expression of an operably linked homologous or heterologous nucleic acid sequence in host cells, such as cells, tissues, organs or whole organisms derived from transformed cell(s).

Host cells are preferably plant cells. Any plant may be a suitable host, such as monocotyledonous plants or dicotyledonous plants, for example maize/corn (*Zea* species, e.g. *Z. mays, Z. diploperennis* (chapule), *Zea luxurians* (Guatemalan teosinte), *Zea mays* subsp. *huehuetenangensis* (San Antonio Huista teosinte), *Z. mays* subsp. *mexicana* (Mexican teosinte), *Z. mays* subsp. *parvighlumis* (Balsas teosinte), *Z. perennis* (perennial teosinte) and *Z. ramosa*, wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc.), sunflower (*Helianthus annus*), tobacco (*Nicotiana* species), alfalfa (*Medicago sativa*), rice (*Oryza* species, e.g. *O. sativa* indica cultivar-group or *japonica* cultivar-group), forage grasses, pearl millet (*Pennisetum* species. e.g. *P. glaucum*), tree species, vegetable species, such as *Lycopersicon* ssp (recently reclassified as belonging to the genus *Solanum*), e.g. tomato (*Solanum lycopersicum*, syn. *L. esculentum*) such as e.g. cherry tomato, var. *cerasiforme* or current tomato, var. *pimpinellifolium*) or tree tomato (*S. betaceum*, syn. *Cyphomandra betaceae*), potato (*Solanum tuberosum*) and other *Solanum* species, such as eggplant (*Solanum melongena*), pepino (*S. muricatum*), cocona (*S. sessiliflorum*) and naranjilla (*S. quitoense*); peppers (*Capsicum annuum, Capsicum frutescens*), pea (e.g. *Pisum sativum*), bean (e.g. *Phaseolus* species), carrot (*Daucus carota*), *Lactuca* species (such as *Lactuca sativa, Lactuca indica, Lactuca perennis*), cucumber (*Cucumis sativus*), melon (*Cucumis melo*), zucchini (*Cucurbita pepo*), squash (*Cucurbita maxima, Cucurbita pepo, Cucurbita mixta*), pumpkin (*Cucurbita pepo*), watermelon (*Citrullus lanatus* syn. *Citrullus vulgaris*), fleshy fruit species (grapes, peaches, plums, strawberry, mango, melon), ornamental species (e.g. Rose, Petunia, Chrysanthemum, Lily, Tulip, Gerbera species), woody trees (e.g. species of *Populus, Salix, Quercus, Eucalyptus*), fibre species e.g. flax (*Linum usitatissimum*) and hemp (*Cannabis sativa*). In one embodiment vegetable species, especially *Solanum* species (including *S. Lycopersicum* species) are preferred.

Thus, for example species of the following genera may be transformed: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Cucumis, Hyoscyamus, Lycopersicon, Solanum, Nicotiana, Malus, Petunia, Digitalis, Majorana, Ciahorium, Helianthus, Lactuca, Bromus, Citrullus, Asparagus, Antirrhinum, Heterocallis, Nemesis, Pelargonium, Panieum, Pennisetum, Ranunculus, Senecio, Salpiglossis, Browaalia, Glycine, Pisum, Phaseolus, Gossypium, Glycine, Lolium, Festuca, Agrostis*. A further preference is for each of *Cucurbita, Brassica, Lycopersicon, Solanum, Oryza* and *Zea*. A preference is for each of *Avena, Medicago, Capsicum, Nicotiana, Lactuca, Pisum, Cucumis, Cucurbita, Brassica, Solanum* (including *Lycopersicon*), *Oryza* and *Zea*.

The construction of chimeric genes, and vectors for introduction of chimeric genes into the genome of host cells, is generally known in the art. To generate a chimeric gene the trichome specific promoter sequence is operably linked to another nucleic acid sequence which is to be transcribed in the host cells, using standard molecular biology techniques. The promoter sequence may already be present in a vector so that the nucleic acid sequence which is to be transcribed is simply inserted into the vector downstream of the promoter sequence. The vector is then used to transform the host cells and the chimeric gene is preferably inserted in the nuclear genome or into the plastid, mitochondrial or chloroplast genome, so that the downstream nucleic acid sequence is expressed due to the activity of the promoter (e. g., Mc Bride et al., 1995 Bio/Technology 13, 362; U.S. Pat. No. 5,693,507).

A chimeric gene, therefore, preferably comprises an trichome specific promoter as described above, operably linked to a homologous or heterologous nucleic acid sequence, and optionally followed by a 3' nontranslated nucleic acid sequence (3'UTR). The homologous or heterologous nucleic acid sequence may be a sequence encoding a protein or peptide, or it may be a sequence which is transcribed into an active RNA molecule, such as an sense and/or antisense RNA (sense and antisense RNA includes for example dsRNA or stem-loop RNA structures) suitable for silencing a gene or gene family in the host cell or organism.

The trichome specific promoter-comprising chimeric gene can be stably inserted in a conventional manner into the nuclear genome of a single plant cell, and the so-transformed plant cell can be used in a conventional manner to produce a transformed plant that has an altered phenotype due to the expression of the chimeric gene.

In this regard, a T-DNA vector, comprising a trichome specific promoter (or variant or fragment as described above) operably linked to a further nucleic acid sequence, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO 84/02913 and published European Patent application EP 0 242 246 and in Gould et al. (1991, Plant Physiol. 95, 426-434). The construction of a T-DNA vector for *Agrobacterium* mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718.

Preferred T-DNA vectors each contain a trichome specific promoter operably linked to the nucleic acid sequence to be transcribed between T-DNA border sequences, or at least located to the left of the right border sequence. Border sequences are described in Gielen et al. (1984, EMBO J 3, 835-845). Of course, other types of vectors can be used to transform the plant cell, using procedures such as direct gene transfer (as described, for example in EP 0 223 247, or particle or microprojectile bombardment as described in US 2005/055740 and WO 2004/092345), pollen mediated transformation (as described, for example in EP 0 270 356 and WO 85/01856), protoplast transformation as, for example, described in U.S. Pat. No. 4,684,611, plant virus-mediated transformation, liposome-mediated transformation (as described, for example in U.S. Pat. No. 4,536,475), and other methods such as those described methods for transforming certain lines of maize (e. g., U.S. Pat. No. 6,140, 553; Fromm et al., 1990, Bio/Technology 8, 833-839; Gordon-Kamm et al., 1990, The Plant Cell 2, 603-618) and rice (Shimamoto et al., 1989, Nature 338, 274-276; Datta et al. 1990, Bio/Technology 8, 736-740) and the method for transforming monocots generally (WO 92/09696). For cotton transformation see also WO 00/71733, and for rice transformation see also the methods described in WO 92/09696, WO 94/00977 and WO 95/06722. For *sorghum* transformation see e.g. Jeoung J M et al. 2002, Hereditas 137: 20-8 or Zhao Z Y et al. 2000, Plant Mol Biol. 44:789-98). For tomato or tobacco transformation see also An G. et al., 1986, Plant Physiol. 81: 301-305; Horsch R. B. et al., 1988, In: Plant Molecular Biology Manual A5, Dordrecht, Netherlands, Kluwer Academic Publishers. pp 1-9; Koornneef M. et al., 1986, In: Nevins D. J. and R. A. Jones, eds. Tomato Biotechnology, New York, N.Y., USA, Alan R. Liss, Inc. pp 169-178). Likewise, selection and regeneration of transformed plants from transformed cells is well known in the art. Obviously, for different species and even for different varieties or cultivars of a single species, protocols are specifically adapted for regenerating transformants at high frequency.

Besides transformation of the nuclear genome, also transformation of the plastid genome, preferably the chloroplast genome, is included in the invention. One advantage of plastid genome transformation is that the risk of spread of the transgene(s) can be reduced. Plastid genome transformation can be carried out as known in the art, see e.g. Sidorov V A et al. 1999, Plant J. 19: 209-216 or Lutz K A et al. 2004, Plant J. 37(6):906-13.

The resulting transformed plant can be used in a conventional plant breeding scheme to produce more transformed plants containing the transgene. Single copy transformants can be selected, using e.g. Southern Blot analysis or PCR based methods or the Invader® Technology assay (Third Wave Technologies, Inc.). Transformed cells and plants can easily be distinguished from non-transformed ones by the presence of the chimeric gene. The sequences of the plant DNA flanking the insertion site of the transgene can also be sequenced, whereby an "Event specific" detection method can be developed, for routine use. See for example WO 01/41558, which describes elite event detection kits (such as PCR detection kits) based for example on the integrated sequence and the flanking (genomic) sequence.

In one embodiment the nucleic acid sequence which is to be transcribed, and optionally translated (if it is a coding sequence), is inserted into the plant genome so that the sequence to be transcribed is upstream (i.e. 5') of suitable 3' end transcription regulation signals ("3' end") (i.e. transcript formation and polyadenylation signals). Polyadenylation and transcript formation signals include those of the nopaline synthase gene ("3' nos") (Depicker et al., 1982 J. Molec. Appl. Genetics 1, 561-573.), the octopine synthase gene ("3'ocs") (Gielen et al., 1984, EMBO J 3, 835-845) and the T-DNA gene 7 ("3' gene 7") (Velten and Schell, 1985, Nucleic Acids Research 13, 6981-6998), which act as 3'-untranslated DNA sequences in transformed plant cells, and others.

In one embodiment the 3' end sequence (or 3'UTR) used is that of a ShzFPS, ShZIS or ShTPS9, such as the 3' end of the gene associated with SEQ ID NO: 4, 3, 1 or 2 or a variant thereof.

The nucleic acid sequence to be expressed is in one embodiment a sequence encoding a protein or peptide, including hybrid proteins or peptides or fusion proteins. The coding sequence may be of any origin, i.e. plant, fungus (including yeast), animal, bacterial, synthetic, viral, human, etc. It may also comprise a sequence encoding a targeting peptide, such as a secretion signal peptide or a plastid targeting signal. A coding sequence may also be linked in-frame to a gene encoding a selectable or scorable marker, such as for example the neo (or nptII) gene (EP 0 242 236) conferring kanamycin resistance, so that the cell expresses a fusion protein which is easily detectable. Although the coding region (cDNA or genomic DNA) of any gene may be used, examples of the coding regions of the following genes are preferably operably linked to a promoter according to the invention:

1. pest or pathogen disease signal transduction pathway genes or pathways, or disease resistance genes or pathways; for example antifungal or antiviral proteins, insecticidal proteins, and the like.
2. herbivore repellent genes or pathways
3. pest, pathogen or herbivore attractant genes or pathways (to generate catch or trap crops)
4. secondary metabolite biosynthesis genes or pathways, including genes for the production of (sesqui)terpenes such as epizingiberene, flavonoids or oils, therapeutic and/or pharmacologically and cosmetically important products or industrially valuable compounds, genes providing nutritional or nutraceutical compounds, flavourants or scents, aromas (herbs), pollinator attractor genes
5. phytoremediation applications e.g. ion and pollutant metal secretion genes (Psaras et al., 2000, Ann Bot 86, 73)

The chimeric genes or vectors according to the invention can also be used to transform microorganisms, such as bacteria (e.g. *Escherichia coli, Pseudomonas, Agrobacterium, Bacillus*, etc.) or fungi or algae or insects, or the genes or vectors may be used to engineer viruses. Transformation of bacteria with nucleic acid sequence of this invention, incorporated in a suitable cloning vehicle, can be carried out in a conventional manner, preferably using conventional electroporation techniques as described in Maillon et al. (1989, FEMS Microbiol. Letters 60, 205) and WO 90/06999. For expression of coding sequences in prokaryotic host cell, the codon usage of the nucleic acid sequence may be optimized accordingly (likewise, for expression of coding sequences in plant cells, codon usage of the nucleic acid sequence may be optimized as known). Intron sequences should be removed and other adaptations for optimal expression may be made as known.

For obtaining enhanced expression of a nucleic acid sequence in monocot plants such as grass species, e.g. maize or rice, an intron, preferably a monocot intron, can be added to the chimeric gene. For example the insertion of the intron of the maize Adh1 gene into the 5' regulatory region has been shown to enhance expression in maize (Callis et. al., 1987, Genes Develop. 1: 1183). Likewise, the HSP70 intron, as described in U.S. Pat. No. 5,859,347, may be used to enhance expression. Thus, one or more introns may optionally be inserted into any of the promoter sequences according to the invention, or into the 5' UTR or the coding sequence.

Encompassed herein are also transgenic plants (and parts thereof) comprising trichome specific promoter, operably linked to a protein or polypeptide encoding nucleic acid sequence, as described further below.

In a different embodiment the promoters according to the invention are used to make a chimeric gene and vector for gene silencing, whereby the promoter is operably linked to a sense and/or antisense nucleic acid sequence of a target gene (endogenous gene or gene family which is to be silenced specifically in trichome cells).

"Gene silencing" refers to the down-regulation or complete inhibition of gene expression of one or more target genes. The use of inhibitory RNA to reduce or abolish gene expression is well established in the art and is the subject of several reviews (e.g. Baulcombe, 1996, Plant Cell 8: 1833-1844; Stain et al., 1997, Plant Journal 12: 63-82; Depicker and Van Montagu, 1997, Curr. Opinion Cell Biol. 9: 373-382). There are a number of technologies available to achieve gene silencing in plants, such as chimeric genes which produce antisense RNA of all or part of the target gene (see e.g. EP 0 140 308 B1, EP 0 240 208 B1 and EP 0 223 399 B1), or which produce sense RNA (also referred to as co-suppression), see EP 0 465 572 B1.

The most successful approach so far has however been the production of both sense and antisense RNA of the target gene ("inverted repeats"), which forms double stranded RNA (dsRNA) in the cell and silences the target gene(s). Methods and vectors for dsRNA production and gene silencing have been described in EP 1 068 311, EP 983 370 A1, EP 1 042 462 A1, EP 1 071 762 A1 and EP 1 080 208 A1.

A vector according to the invention may therefore comprise a trichome specific promoter operably linked to a sense and/or antisense DNA fragment of a target gene. Short (sense and antisense) stretches of the target gene sequence, such as at least about 17, 18, 19, 20, 21, 22, 23, 24 or 25 nucleotides of coding or non-coding sequence may be sufficient. Longer sequences are frequently also used, such as at least about 100, 200, 250, 300, 400, 500, 1000, 1500 nucleotides, or more. Preferably, the sense and antisense fragments are separated by a spacer sequence, such as an intron, which forms a loop (or hairpin) upon dsRNA formation. Any stretch of the target gene may be used to make a gene silencing vector and a transgenic plant in which the target gene or gene family is silenced. A convenient way of generating hairpin constructs is to use generic vectors such as pHANNIBAL and pHELLSGATE, vectors based on the Gateway® technology (see Wesley et al. 2004, Methods Mol Biol. 265:117-30; Wesley et al. 2003, Methods Mol Biol. 236:273-86 and Helliwell & Waterhouse 2003, Methods 30(4):289-95.), all incorporated herein by reference.

By choosing conserved nucleic acid sequences of the target gene, the family members in a host plant can be silenced in trichome cells.

Encompassed herein are also transgenic plants comprising trichome specific promoter, operably linked to a sense and/or antisense DNA fragment of a target gene nucleic acid sequence and exhibiting a target gene silencing phenotype. The phenotype will depend on the function of the gene, and may be a chemical or molecular change, macroscopically visible or not visible. Such chimeric genes and vectors can, therefore, also be used to determine or verify the function of genes in trichomes.

The chimeric genes according to the invention may be introduced stably into the host genome or may be present as an episomal unit.

Transgenic Cells and Organisms According to the Invention

Transgenic cells and organisms, especially plants, plant cells, tissues or organs are provided, obtainable by the above methods. These cells and organisms are characterized by the presence of a chimeric gene in their cells or genome by the presence of a promoter according to the invention. In addition, the mRNA transcript or the translated protein, may alter the phenotype of the cells or organism, e.g. of the plant trichomes, especially the glandular trichomes.

In one embodiment the chimeric gene introduced into the plant is composed of parts which all occur naturally in the host genus or species, e.g. if a host plant of the genus *Solanum* is to be transformed, preferably the promoter according to the invention from the genus *Solanum* is used and operably linked to a nucleic acid sequence also from the genus *Solanum* and optionally a 3'UTR from the genus *Solanum*. The same can be applied to the species of the host. Although the plant will carry a transgene, all nucleotide elements thereof are naturally found in the host genus or species (albeit not in this combination), reducing regulatory problems and improving public acceptance.

The position of the chimeric gene in the genome can affect the activity of the promoter and the expression level of the chimeric gene. Therefore, transformants ("Events" or "Transformation Events") expressing high, constitutive levels of the protein or of the sense and/or antisense transcript (when silencing constructs are used) can be selected by e.g. analysing copy number (Southern blot analysis), mRNA transcript levels (e.g. Northern blot analysis or RT-PCR) or by analysing the presence and level of protein encoded by the nucleic acid sequence (e.g. SDS-PAGE followed by Western blot analysis; ELISA assays, immunocytological assays, etc). The transformants can also be tested for the stability of expression under one or more biotic and/or abiotic stress conditions and those events which retain high, constitutive expression under one or more of the desired conditions can be identified and selected for further use.

The transgenic plants can be used in traditional breeding methods, such as crossing, selfing, backcrossing, etc. By selfing the transformants, plants which are homozygous for the transgene can be generated. Breeding procedures are known in the art and are described in standard text books of plant breeding, e.g., Allard, R. W., Principles of Plant Breeding (1960) New York, N.Y., Wiley, pp 485; Simmonds, N. W., Principles of Crop Improvement (1979), London, UK, Longman, pp 408; Sneep, J. et al., (1979) Tomato Breeding (p. 135-171) in: Breeding of Vegetable Crops, Mark J. Basset, (1986, editor), The Tomato crop: a scientific basis for improvement, by Atherton, J. G. & J. Rudich (editors), Plant Breeding Perspectives (1986); Fehr, Principles of Cultivar Development—Theory and Technique (1987) New York, N.Y., MacMillan.

Transgenic cells or organisms can also be used in cell cultures (plant cell cultures, bacterial or fungal cell cultures such as yeast cultures, human or mammalian cell cultures, insect cell cultures), for example for the large scale production of recombinant proteins. In one embodiment a cell culture is provided, comprising cells comprising a promoter according to the invention.

Methods and Uses According to the Invention

Also provided is a method for making a transgenic plant or plant cell, comprising the steps of:
- (a) generating a chimeric gene or a vector comprising a promoter according to the invention, operably linked to a nucleic acid sequence to be expressed;
- (b) transforming a plant or plant cell with said chimeric gene or vector; and, optionally,
- (c) regenerating a transgenic plant or plants.

In an embodiment of this method, a vector comprising a promoter of the invention is used in step a), and said vector comprises the nucleic acid sequence of SEQ ID NO:1, operably linked to a nucleic acid sequence encoding an amino acid sequence of SEQ ID NO:5 (ShzFPS) or a variant thereof having at least 80% identity to the amino acid sequence of SEQ ID NO:5, said amino acid sequence having farnesyl-diphosphate synthase activity. Said variant of SEQ ID NO:5 may have at least 80%, 85%, 90%, 91%, 92%, 93%, 94%, 95%, 96%, 97%, 98%, or 99% sequence identity to the amino acid sequence of SEQ ID NO:5, preferably over the full length.

In an embodiment, a second vector comprising a second promoter of the invention is used in step a), and said second vector comprises the nucleic acid sequence of SEQ ID NO:2, operably linked to a nucleic acid sequence encoding an amino acid sequence of SEQ ID NO:6 or a variant thereof having at least 92% identity to the amino acid sequence of SEQ ID NO:6, said amino acid sequence having zingiberene synthase activity. Variants of 7-epizingiberene synthase (SEQ ID NO:6) include, for example, proteins having at least 92%, 92.5%, 93%, 93.5%, 94%, 94.5%, 95%, 95.5%, 96%, 96.5%, 97%, 97.5%, 98%, 98.5%, 99%, 99.5% or more, such as 100%, amino acid sequence identity, preferably over the entire length, to SEQ ID NO:6.

It is to be noted that the vector and the second vector may be combined into a single vector for the purposes of the present invention.

Thus, both the ShzFPS gene and the ShZIS gene are preferably expressed in a transgenic plant or plant cell under control of their own promoter. In an embodiment, the amino acid sequence of SEQ ID NO:5 and/or SEQ ID NO:6 are preceded by a targeting sequence, e.g., for targeting of the Z,Z-farnesyl pyrophosphate synthase and/or the 7-epizingiberene synthase to intracellular organelles such as plastids, preferably chloroplasts, or mitochondria, or for secretion from the cell. Targeting to plastids is particularly attractive as overproduction of sesquiterpenes in the cytosol is usually toxic to cells, whereas overproduction of sesquiterpenes in plastids does not suffer from this problem. The targeting sequence may be the natural targeting sequence of said Z,Z-farnesyl pyrophosphate synthase (as set forth in SEQ ID NO:7) and/or the natural targeting sequence of the 7-epizingiberene synthase (as set forth in SEQ ID NO:8). Alternatively, other targeting sequencing may be used. The skilled person will be capable of selecting a suitable targeting sequence if required.

Preferably, said plant or plant cell is not a *Solanum habrochaites* plant or plant cell.

The invention also pertains to a transgenic plant or plant cell obtainable by the method set forth herein. In an embodiment, said plant or plant cell is not a *Solanum* habrochaites plant or plant cell. Preferably, said plant or plant cell is a *Solanum lycopersicum* plant or plant cell.

The regenerated plant (or progeny thereof which retain the transgene) or parts thereof may be used for various purposes, such as in agriculture as such or for molecular farming. The further use depends on the phenotype conferred by the transgene. For example, if the transgenic plant produces high levels of a secondary metabolite in the trichomes, the plants will be grown and the metabolite harvested. Thus, all or part of the plants may be harvested for either human or animal consumption or for industrial purposes, depending on the transgene. Also, different parts of the plant may be harvested for different purposes, e.g. the fruit or seed may be harvested for consumption, while the leaves, stems and/or flowers may be harvested for industrial purposes.

Obviously, the phenotype conferred by the transgene can be tested, e.g. in field trials (e.g. disease or pest resistance tests can be carried out using conventional methods).

Transgenic plants may be identified which provide constitutively high promoter activity in trichomes under non-stress conditions, and whereby the promoter activity remains essentially unchanged (is at least not reduced, or not reduced significantly) when the plant is exposed to one or more biotic and/or abiotic stresses.

The plants may be used in conventional agricultural and breeding methods.

The following non-limiting Examples describe the use of promoters according to the invention. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. All literature cited herein is herein incorporated by reference.

SEQUENCE LISTING

Figure 1:
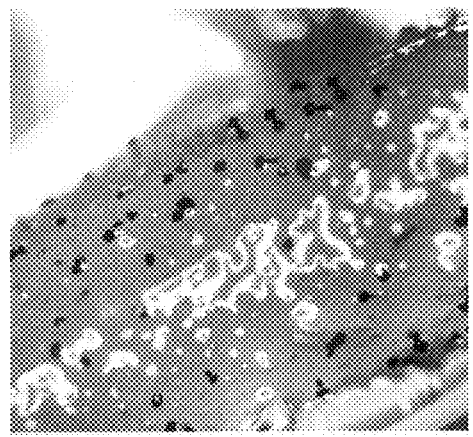
FIG. 1 shows trichome-specific GUS staining of a *Solanum lycopersicum* plant that was transformed with pTPS9:GUS. It shows that the TPS9 promoter was specifically active in trichomes of *S. lycopersicum*.

SEQ ID NO: 1: ShzFPS promoter sequence.
TGGCCATTACGTGGACTAATTTTTTTACAATAAATGATCACTTTATTTTTAACAAG
TATGATTAATAATTAATTGAAATTAGTGAGTTTGAAATTTGACTTTTGTTTAGCCT
ATGAGCAAACCTTTAAAGTTAATTCAAAATTAAAAGTTATTGATTTTTAATCATGT
TTATGAATCAAATGTGATCAAAAGGTCAAAATCAACTGTCTCCCAAATAATTTTTT
TAAACTCGAGATGATTTGAAATTTTTTCAACCAATAGTTATATTTTCCAATGTCA
TATTATTAAAAACTTGAGGCTAATTCCATCCTGGAATTTATGACTATAGTTATAGT
TATCTTAGACTCTTAGCTGCGTTATAGTCAGACTTGATAATTATTAAAAAGTGTGT
GACTCTGATTTTTCACATATGACGATTTGAGAAATTGATAATCTAGAAAGCTATAT
CATGAAAAATTCTAAGAATGATTGAAGATAATAAGAATATTTTGAAATATCGCAA
CCCTACCACAAAGTTTTACCAACCTATTTTCTTTTATATAGATATGAGCTATATGA
CACATGGAAATACAATTATAAAGCAGTAGTTAGAGGTGAATTAATATTGAATTTT
AAAGGGAATAATCAATGGATGATATCTTTTTTACTTTTTTTTCTTTTATCACTAAAA
GTGCATTCATTGTAGACTAAAACACATTAAATAGAGTTTTATATCCTTTTCTCATA
CATGGTCCCTCATTTTCTTCTTAGTCTTGTATTATAAGTCACCTCTTTTTAAAAATA
ATTGGATCATAATATATGTTATTTTATAAAATTTATGCATAAAATATCATATTTTG
CTCATTATATTTTTATTGATTAATTAATAATCTTAAAATATATTTATTTTGACTGAT
CTTGAAAATCAATAACTAATTAAATAAGGGCATAGAAATAAAATTATCTTATTTCT
TGTTACAAGTACAAATACAAAAAGTGACTTATAATATGGGACGGGGGGAGTAATT
AAGTGAAAGGTTATTCGTTCTTTATTGGTATTATCAGTTATTTAGGAGATAACTGA
TTTAGCAATTTTTAGTCTTTATTTATTTTATACACAGTTTATAAAACATACTTACAT
TTTTGAACTTGGTGATGGCGTAGCCCAGGGGTGTTAAATGGGCGGGTTGGGTTGA
AATTGGAAATATTACTATGGGTGAATAGAAATTGGGTTGGGTTTGACCCGCCCAA
ATTTACTTTGGGCTCAAATGAGCTAAAATATGGGTTGGGTCTTGACCCGCTCAATT
TGACCCGCTTAATCTTAGTTATTTAACATATTGATATTTAATTTTTATAATCACAAT
TTGAATCTCCGTTCAAGAATTTTTTTTTATAATAAAAGTAACAAATGGATAGATA
AATCATAAAAAAAAAGCAACAAATCGATAATAATTCATACTGTAAATATAGGAAC
ATATCTTAATACTAAGTTATAAAACAGGTTGAAATTAGTAATTGAATTGGGCTCA
ATTGAGAATTCTCTTCAAATAGGTTAAGCTTGAATGGGTTGAGGTTGAACCCAACT
CAAATTATCTTGAGCTCAATCCTTAAAATTCTGAGCGTATTGGGCATGTTACCATG
TTTGGGTTCATTTTTAACGCCCCTAGCGTAGTCGAAAGAAGTCAATCCATGAGGTT
TGTAAAACAAATGCGAATAATTTACTCTACCATTGAGCTTGTTAGTCATATGGTGT
AGCAAAATGGTAGATTATCGAAAAAATATCTTAATTATGCTTCATAGTTATAATTT
GTTAATTACAATTAGTAGCTACATGTTATATGGAGGAGAGTGGCGAGCGAGATTG
GGAGAGGAAAGAGAGAAGTGAGTGAGACAAGGTAGAGAGTGGGAGAGAGGCGA
ACTGCATATGCATATTTGTCAAAATAATTGTATATATGTAACTGGTATACATACGT
ATTCGTATATCTGGTGAGTGAGGAGAGAAAAGAGAGAAGCGAGCGAGATTGGAA
GAGGAAAGAGAGAGCCGAGCGAGAGAGGACAATAATTTATGTAATTCGCATCTC
ATTTGTATAATTAATTTTGTTCGAAATGCGGTTCAATATAATTTTTTAACCATAAG
CATAAACAACCCTATATAGAACTATTGATCAATATAGAACTATTGATCTATTGATC
AAAAGAGTCATACCATAATTCTATTTAAACACCACCTCCCTTGTTTCACTTCACAA
TAAAATAAATTTGAGTAATAAAGC SEQ ID NO: 2: ShZIS promoter sequence.
CTCTCTCTAAAGAAGTTGAAGATACCTTCTTCCAGTAAGTGGGACTGGAGGGGGA
GATTTGTTGAATCCATCCCATTTTTTTTGGTCAACTTTAGCTACTCAATTGGTACAA
GCAATTGTTAAAAAGGAATAGTAATTGGAGTTGAAAAGAAAAGATTTGGTAGTTG
GCAAATTGGTAAGATTTGCAACCATTTTTGACTTTGCTATGTTTACATATGTCATT
AGTGACATAGGTATGGTTTTATCCTTCTATAAATAGCGCACTCTTGCTCATTTGTA
GAACACACCAAGTTAGAGAGAAAAACAATTTTGAGAGCAAAGTGAGGTATTCCA
TAGACTATATAAGAAAATAGTCTGTGAAGAAAAATAGAGTGTGAGCGATATTTTA
GTAAGACGGAAACCAAAAGAGTGTTGTTCCTTTTGAGTGTGTAGTAGTCACTTTG
AGTATTGTATTCGTGACTACACAGTGTAAAATTCCTTACTATAGTAATATCAATTG
CTCCTCTTAGTCCGCGGTTTTTTCCCTTATTCAGAAGGGTTTCCACGTAAAATTCTT
GGTGTCATTATTTTCCCATTTTATTTCCATTACTTTTACCATATATACTTTGTGCTT
GTCCGCGTTTTCCCAACAAGATGGTGTTTAAATAGAATTATGGTATGACTCTTTTG
ATCAATAGTTCTATATAGGGTTGTTCATGCTTATGGTTAAAAAATCATATTGAATC
GCATTTCGAATCAAAATTGATAATACAAATGAGATGCGAAGCTTGCATGAGTTCC
AAAAAATATAAATAACGGTAAAATGGTAAAGTTACATCATTTTTAATGCAACTG
CAAAGTAAAAATATAACATATAAAATGAGACAGAGGAAGTATGTAAAATCAATA
ATGAATATGTATTACTCCCTCTATTTCATAATAACTTAAGCTTTGAAGTGTTTCAC
ACCCTTTAAAAAAAGTAGGTTAGGACATAAATGAACATAATTTTTCATTTTTGTCC
TTATTAATTATTGTCAAAAATAACTAAACATTAATTATAATAACTAATtCCAATACT
AACTTAATGGGTAAAATTAGAAGAAATTTTTAAAATAGTCTTGAAAATTTAAAA
CATAAGTTAATTGAAAAATGGAAAGAAAAAAAAAGCTCAAATCTTGTTATTATGTA
ATGGAGGGAGTATTAGACAGAGAAATTATTAATTRCTCCCTCCGTCCCATATTATA
AGTCACTTTTTTCATTTGTACTTGCAACAAGAAATAAGATAATTTTATTTCTATGCC
CTTTGTTATAGATTTTCAAATTAGTCAAAGTAAATATATTTTCAAAAYTAATTAA
TTAATCAATAAGGATATAATGAGCAAAATATGGTATTTAGTATAAATTTATAAAT
ACATATATTATGATCAATATTTAGAGAAGGTGACCTATAATATGAAGGAAGAAAT
GAGGACCATATATGAGAAAGGATATAAACTCTATTTAATGTGTTTAGTGTACAAT
GAATGCACTTTAGTGATAAAGAAAAAAGTTAAAAAAAATATCATCCATGATTATTC
CCTTTAAAATTCGATATTAGTTCACCTCTAACTACTTACAATAATTGTATTTCCATG
TGTCATATAGCTCATATTTATATAAAGAAAATAGGTTGGTAAAACTTTGTGGTAGG
TTTGAGATATTTCAAAATATTCTTATAATTTTTCAATTATTCTTCCAATTTTTTCAT
GATATAGCTTTCTAGATCATCAATTTTCTTAAATCGTCATATGTGAAAATTGGAGT
CACACACTTTTTAATAGTTATCAAGTTTGACTATAGCGCAGCTAAGAGTCTAAGAT
AACTATAACAATAATCATAAATTACAGGATGGAATTAGCCTCAAGTTTGTAATAA
CATGACATTCGAAAATATAACCATTGGATAAAAAAAATTTCAAATCATCTCGAGT

```
TTATAAAAATTATTTGAGAGACAGTTGATTTTGACCTTTTGATCACGTGTGATTCA
TAAACATGATCAAAAATCAACAATTTTTAATTTTTAATTGACTTTAAAGGTTTGCT
AATAGGCTAAACGGAAGTCAAATTTCAAACTCACTATTTCAATTAATTATTAATCA
TACTATGTTAAAAATAGTCCACGTAATGGCCAACAACTAGCAAAACTTATCACGA
GATTCTATATGATACTATATATGCTTTGTTTTTTCGATATTCATTTTATTTAAAGTT
TGATATTTATATTAAAATTAAAATAGATTTTAAATTTGTATTAAGAAAATTCATTA
TAAAAGGTTGAAACATTTTCTAACAAAAAGATATGATGTCCACTTGAATCAAAGA
GTAATAATGCTCATATACTTTTTCTGCTTTGAAATAAGATATGCGATAATGATTGA
CTAATAAAAATTAAAGACTAGTCATTTATAGGGCAAAACGTGCATTTTTACATTTA
ATTACACATCAAGKTTATACCAAAGTGAGATATTATAAGGAAAAATCTTTGTGGC
CAAAATTTTTGGACAGAACGATATTTTATTTATGTTATTTTAATTTTAATACATTTT
AACTACAAAATGGAAAAAATAACAGTTTATTATAAAATAAAAAAAATATTTTAGTT
TTTTTATTTTTTAGTCAATTTTTCTAGCCATTTAGCTCTTTCCATATTATAATATA
AAGAGAAAAGTATTTAAATATCTCTAAATTTGGTGTGAATTAATAGGTTTGTCTC
CGAATTATTGACAACATTAAAACTACTCTCTACTTGACAAATTGAACTTAAACATA
TATACCCTTGATCTTGTCACATCAGTGATATACAATCCCAAATTCTCGTCAACTTT
AGGGGTATTTTGAACACTTCTTTTGACATTTTATTAAGAGTCTCACGTTCCTACAA
GAGTTTGAGACTACTTGATATGCCATGTGGCAGACTGGAGTGTATTTTAAGTTCAG
TTAGTCAACTAAACAATTTTTTTAGAGTAAATTTTAGGTTTAACAAACATAAAAAT
CATATATGTATGTTAATAATTATAGTTGGTATAATTGCGCTTCATAGCAAACTTTA
TGTTTGCTATGACTATTAATTTGTATATTTTGATATACATATACAAAAGAATGAAT
TGTATAATCTCTATTTGTATAAAGCGAGAACGAGAGAAGACAAATGAAAACTGGT
AGCGAGAAATGGAGAGTGACGAAAGACAACTGTTTAATTTGAATCAATGATTTGC
TATTTTATACATTTTTTCCTTATTTTTAAGACTATCAATAATTGAGTGACGAAATTA
ATAATTTGCATTAAATTTAATTAAAAATATTTTCAACATTTCTCTCCGCTAAATATT
TATTTATAACGAGGAAACAAAATCAAAGACAAACACAAAATAGGAGAAATTTCTT
CATTTTTGACCCCTCCACTCCCAAAAACAACACACAATATTCAAGG

SEQ ID NO: 3: ShTPS9 promoter sequence.
TTATTTCACTAATTAAATTTATTCTTAAATATTTATATATATTTATTTTGCTATGCT
AATTTATTTTTTTATAATAAAATTAGTTGAGTGATTTGATGGATACAAAGTCATA
AATTGAATGACTTAACTAAATAAATTATTAAAGTTGAATGATATTATTGATAAAA
AGACATAAATTGAATAATTTTTTTGATATAAAATAAAGTTCAGATATTGTTACACA
ATTAACCATCCTTTTCAATTTTAATAAATAAACTCCTCTTTAATATCGTTCTAATGA
AAATTTCTTCCAAACAACATAAATAATAAGTTCATCATTTATCGACTAATTCATAA
ATATTATTTGAGTAATATCTATGCAATTTTTTACAATGTTTATATTATGTCATTTAA
AAGATAAGGACAGATGCCGGTAAGCATTACAATAAGTGGTAGTAACTACATTATA
AATAGGCCCATCCAATTAGCATAACTTAAACCCACAAATTAAGCTTGAAAAAAAA
AGAGCAAACCTTAGAACAAACAAGCA SEQ ID NO: 4: ShTPS9 promoter sequence (long).
TTTAAATTTTATATTTATATTAAACATTTTATTAATATATATATATATATAGCTATA
AACTCAATAATTACGATGACTTACTATAAATTCGATTTTAAGTTTGAACTCAAAAA
TTCTTAAAACTCTAATTCTACTTGTGTATTCATCTAGCCTCTTATGACACGTaAAAA
AAAATACAATAAATAAATTGCAATAACTCAAATTATTTATATGTGACATAAAGAA
TCGTGTGGCTCTAAAATTTTATTTCTCTGCGGTCCAATTAAAGTTTTGATAATCCAC
CAAATTGAAGACTTAAAATGCCTTATTGAGGTGCCAAATACTAATGAAGAAGAAA
ACAAAACAAAATAAAAACACCTACTCATAAATTATAATATAACTGTATCTCATTG
CTAATATGACATTTAATAGGAGAGTATGAAAATCGATAATTAGGATATATTGTTA
ATATATAATCAAACGTTTTATTTCTTCCTAGTGGTAGAGTAAGGTTCTAATCTAGA
GCCCCTATCCCCTTACCATTACTGTTTAGTATTATGCAAGTTATTTTTTTACTTTGA
TTATCTCTAATATTTTTACTGTCGTTATTTTTGTTTTTTTAATATAATTTTTGTCATA
TTTTTTGCTGTTACAATACTTTCAAATCATGTTTTGAAGAATGATTTCTTGATCCGA
GGATCTATAGTAAACATTCTTTCTATCAAATAAAGATACATATAACTTATAAGGTC
TGCATACATAATACTATCCTTCTCAAACCCCACTTATATGAAATGATACCAGATGA
CTGAGTCAATATCTCAAAAGGTCACTCAAGTTTAAGAATATATCTAGTAAAGTTAT
TAAACTTTCTTTACTATCAATAAAATCACTTAACTTAGATACGTGGATCAATAAAA
TCACTCAACTCAATTTATCATTAAAAAATTATCATAGATAAATAATTTTTTATGC
CATGTAAATATGAACTCCATAAATTAATAAAATTAAAAAAAATCCATCAAGACTT
TTTTATGAATAAACTTAATAATTTATTAGGATATTATTATATAATTCTAATGTATTA
TTACGAGCTTATTAAGAAAAAGTTAGGGTATTGTATGGTAAATAATTGGGGGTA
CATGATTTTATCATATAAAAATATATAGACATTGGCTTAATAACTCTAACTCTGC
AAATATTACTCTGTTACGATCATTAAATTATAAAAATAAATTGACGTCTTATAATT
ATTTTTCGTTGCAATCATTAAGCCCTATGACAATATCAGTATATAGTAATTGGTAA
TGTAACATTCATTCTGATACCAATTTTAAGTGCATAATAATATTATATTAATATTT
ATTTCACTAATTAAATTTATTCTTAAATATTTATATATATTTATTTTGCTATGCTAA
TTTATTTTTTTATAATAAAATTAGTTGAGTGATTTGATGGATACAAAGTCATAAA
TTGAATGACTTAACTAAATAAATTATTAAAGTTGAATGATATTATTGATAAAAAG
ACATAAATTGAATAATTTTTTTGATATAAAATAAAGTTCAGATATTGTTACACAAT
TAACCATCCTTTTCAATTTTAATAAATAAACTCCTCTTTAATATCGTTCTAATGAAA
ATTTCTTCCAAACAACATAAATAATAAGTTCATCATTTATCGACTAATTCATAAAT
ATTATTTGAGTAATATCTATGCAATTTTTTACAATGTTTATATTATGTCATTTAAAA
GATAAGGACAGATGCCGGTAAGCATTACAATAAGTGGTAGTAACTACATTATAAA
TAGGCCCATCCAATTAGCATAACTTAAACCCACAAATTAAGCTTGAAAAAAAAAA
GAGCAAACCTTAGAACAAACAAGCA
```

SEQUENCE LISTING

SEQ ID: 5: *Solanum habrochaites* Z,Z-farnesyl-diphosphate synthase
(zFPS) amino acid sequence.
ARGLNKISCSLSLQTEKLCYEDNDNDLDEELMPKHIALIMDGNRRWAKDKGLDVSEG
IIKIILFPKLKEICDISSKLGIQVITAFAFSTENWKRAKGEVDFLMQMFEELYDEFSRSGV
RVSIIGCKTDLPMTLQKCIALTEETTKGNKGLHLVIALNYGGYYDILQATKSIVNKAM
NGLLDVENINKNLFDQELESKCPNPDLLIRTGGVQRVSNFLLWQLAYTEFYFTKTLFP
DFGEEDLKEAIINFQQRHRRFGGHTY SEQ ID NO: 6: *Solanum habrochaites* 7-epi-zingiberene (ZIS) amino acid
sequence.
CSHSTPSSMNGFEDARDRIRESFGKVELSPSSYDTAWVAMVPSKHSLNEPCFPQCLDW
IIENQREDGSWGLNPSHPLLLKDSLSSTLACLLALTKWRVGDEQIKRGLGFIETQSWAI
DNKDQISPLGFEIIFPSMIKSAEKLNLNLAINKRDSTIKRALQNEFTRNIEYMSEGFGEL
CDWKEIIKLHQRQNGSLFDSPATTAAALIYHQHDKKCYEYLNSILQQHKNWVPTMYP
TKIHSLLCLVDTLQNLGVHRHFKSEIKKALDEIYRLWQQKNEEIFSNVTHCAMAFRLL
RISYYDVSSDELAEFVDEEHFFATSGKYTSHVEILELHKASQLAIDHEKDDILDKINNW
TRTFMEQKLLNNGFIDRMSKKEVELALRNFYIISDLAENRRYIKSYEENNFKILKAAYR
SPNINNKDLFIFSIRDFELCQAQHQEELQQLKRWFEDCRLDQLGLSEQFISASYLCAIPI
VPGPELSDARLVYAKYVMLLTIVDDHFESFASTDECLNIIELVERWDDYASVGYKSER
VKVLFSMFYKSIEEIATIAEIKQGRSVKNHLINLWLKVMKLMLMERVEWCSGKTIPRI
EEYLYVSSITFGSRLIPLTTQYFIGIKISKDLLESDEIYGLCNFTGIVLRLLNDLQDSKRE
QKEGSINLVTLLMKSISEEEAIMKMKEILEMKRRELFKMVLVQKKGSQLPQLCKEIFW
RTCKWAHTTYSQTDRYRFPEEMENHIDEVFYKPLNH SEQ ID NO: 7: *Solanum habrochaites* Z,Z-farnesyl-diphosphate synthase
(zFPS) targeting sequence (amino acid sequence).
MSSLVLQCWKLSSPSLILQQNTSISMGAFKGIHKLQIPNSPLTVS SEQ ID NO: 8: *Solanum habrochaites* 7-epi-zingiberene (ZIS) targeting
sequence (amino acid sequence).
MIVGYRSTIITLSHPKLGNGKTISSNAIFRRSCRVR

Examples

Selection of Gene for Promoter Isolation

Figure 2:
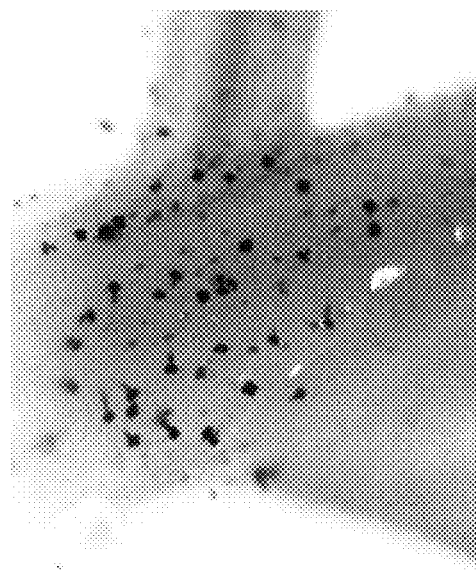
FIG. 2 shows trichome-specific GUS staining of a *Solanum lycopersicum* plant that was transformed with pzFPS:GUS. It shows that the zFPS promoter was specifically active in trichomes of *S. lycopersicum*.

Trichome-specific cDNA libraries of *S. lycopersicum* and the wild tomato *S. habrochaites* were sequenced using next generation sequencing technology (Illumina HiSeq 2000). The TruSeq kit (Illunima) was used to prepare the cDNA libraries. Upon sequencing, the data analysis showed that the frequency of reads for *S. habrochaites* farnesyl diphosphate synthase (ShzFPS; FJ194969), *S. habrochaites* zingiberene synthase (ShZIS; JN990661), and *S. habrochaites* germacrene synthase (ShTPS9; JN402388) was very high compared to other known trichome-specific genes expressed in the trichomes of *S. habrochaites* (LA1777 and PI127826) and *S. lycopersicum* (e.g., ShMKS1 and SlMTS1; see Table 1). Subsequently, RNA of different tissues of *S. lycopersicum* CV Moneymaker and the wild tomato *S. habrochaites* was isolated. Tissue specific expression levels of ShzFPS, ShZIS and ShTPS9 were tested in several different plant organs including trichomes. Expression of the ShzFPS, ShZIS and ShTPS9 gene was much higher than that of other well-known trichome-specific genes (e.g., ShMKS1 and SlMTS1; Table 1). Moreover, it was shown that expression of ShzFPS and ShTPS9 was trichome-specific (FIGS. 1 and 2).

TABLE 1

The number of reads/transcripts that map to the following genes as a % of the total number of reads/transcripts in the library.

| Genes | S. hab LA_1777 | S. hab PI127826 | S. lyc LA_4024 |
|---|---|---|---|
| ShzFPS | 0.2354 | 0.1939 | n/a |
| ShZIS | 0.1406 | 0.1929 | n/a |
| ShTPS9 | 0.0563 | 0.0036 | n/a |

TABLE 1-continued

The number of reads/transcripts that map to the following genes as a % of the total number of reads/transcripts in the library.

| Genes | S. hab LA_1777 | S. hab PI127826 | S. lyc LA_4024 |
|---|---|---|---|
| ShMKS1 | 0.0058 | 0.0002 | n/a |
| SlMTS1 | n/a | n/a | 0.0001 |

Promoter Sequence Isolation

To obtain promoter sequences a genomic walk on genomic DNA was performed according to the Clontech GenomeWalkerUniversal kit. Total genomic DNA was isolated from *S. habrochaites* PI127826. Two µg of gDNA was digested separately with several 6-base recognition blunt cutting restriction enzymes, followed by adaptor ligation and dilution. First round of amplification was performed with Adaptor Primer1 and a gene-specific primer. Subsequently, secondary nested amplification was performed with Adaptor Primer2 and a nested gene-specific primer. Additional rounds of nested amplification were performed. The amplified PCR fragments were cloned and Sanger sequenced.

A nested PCR on the different genomic DNA fragments with adaptor and specific primers resulted in novel promoter sequence fragments. Cloning of PCR products was performed with the Original TA Cloning® Kit from Invitrogen using plasmid pCR® 2.1. After sequencing, new reverse primers could be designed on the novel promoter fragment sequence. A PCR on genomic DNA with primers containing appropriate restriction sites for cloning resulted in the final DNA regulatory nucleic acid fragments.

Based on the 5' sequence information of nucleic acid sequences as depicted in GenBank accession nos. FJ194969 (ShzFPS), JN990661 (ShZIS) and JN402388 (ShTPS9) specific reverse primers were designed.

Primers Kit:

```
Adaptor Primer 1 (AP1; 22-mer)
                                          (SEQ ID NO: 9)
5'-GTAATACGACTCACTATAGGGC-3'

Nested Adaptor Primer 2 (AP2; 19-mer)
                                          (SEQ ID NO: 10)
5'-ACTATAGGGCACGCGTGGT-3'
```

Primers Used for Genomic Walk for ShzFPS Promoter (SEQ ID NO:1)

| Primer name | 5' - 3' sequence |
|---|---|
| Round 1 | |
| Intron 1 of ShzFPS | GTGTACGTATATAAGGTATGAACAAAAACTAC (SEQ ID NO: 11) |
| Nested primer | CTAAAGTAATTAATTCCCATAAGTAATTAAC (SEQ ID NO: 12) |
| Round 2 | |
| Promoter primer1 | GATTGACTTCTTTCGACTACGCTAGGGGCG (SEQ ID NO: 13) |
| Nested primer | CCCAAACATGGTAACATGCCCAATACGCTC (SEQ ID NO: 14) |
| Round 3 | |
| Promoter primer2 | CTCTATTTAATGTGTTTTAGTCTACAATGAATG CACTTTTAGTG (SEQ ID NO: 15) |
| Nested primer | CAAGACTAAGAAGAAAATGAGGGACCATGTATG AGAAAAGG (SEQ ID NO: 16) |

Primers Used for Genomic Walk for ShZIS Promoter (SEQ ID NO: 2)

| Primer name | 5' - 3' sequence |
|---|---|
| Round 1 | |
| Exon 1 of ShZIS | CATTGATGAAGGGGTACTGTGGC (SEQ ID NO: 17) |
| Nested primer | TGCATCTTACTCTACATGATCTC (SEQ ID NO: 18) |
| Round 2 | |
| Promoter primer1 | CGAGAATTTGGGATTGTATATCACTGATGTGACAAGA TCAAG (SEQ ID NO: 19) |
| Nested primer | GTAGAGAGTAGTTTTAATGTTGTCAATAATTCGGAGA CAAACC (SEQ ID NO: 20) |
| Round 3 | |
| Promoter primer2 | CAAAGCATATATAGTATCATATAGAATCTCGTGATAA GTTTTGC (SEQ ID NO: 21) |
| Nested primer | GTGATAAGTTTTGCTAGTTGTTGGCCATTACGTGGAC (SEQ ID NO: 22) |

Primers Used for Genomic Walk for ShTPS9 Promoter (SEQ ID NO:3)

| Primer name | 5' - 3' sequence |
|---|---|
| Round 1 | |
| Primer exon 1 ShTPS9 | CGTAAATGGATATGTATCTCCTTGCTTC (SEQ ID NO: 23) |
| Nested primer | GCTTCACTAACTTCAACCTTAAGAGAG (SEQ ID NO: 24) |

Primers Used for Genomic Walk for ShTPS9 Promoter Long (SEQ ID NO:4)

| Primer name | 5' - 3' sequence |
|---|---|
| Round 1 | |
| Primer exon 1 ShTPS9 | CGTAAATGGATATGTATCTCCTTGCTTC (SEQ ID NO: 23) |
| Nested primer | GCTTCACTAACTTCAACCTTAAGAGAG (SEQ ID NO: 24) |
| Round 2 | |
| Promoter primer1 | GAAAAGGATGGTTAATTGTGTAACAATATCTGAACTTTA TTTTATATC (SEQ ID NO: 25) |
| Nested primer | GTTAAGTCATTCAATTTATGACTTTGTATCCATCAAATC ACTCAAC (SEQ ID NO: 26) |

The promoter sequences obtained are set forth below.
Trichome-Specific Promoter Sequences
SEQ ID NO 1: 2254 by ShzFPS promoter
SEQ ID NO 2: 3451 by ShZIS promoter
SEQ ID NO 3: 530 by ShTPS9 promoter
SEQ ID NO 4: 1875 by ShTPS9 promoter long
Transformation Constructs Final ShzFPS and ShTPS9 promoter sequences (SEQ ID NO: 1 and 4, respectively) were placed in front of the GUS-A marker gene in the pKG1662 vector. Promoter and marker gene were subsequently shuttled into the multiple cloning site of the binary pBIN-plus vector (Van Engelen et al., 1995, Transgenic Res, 288). These constructs were incorporated into *Agrobacterium tumefaciens* GV3101 and used to transform tomato *S. lycopersicum* var. Moneymaker, according to the method described by Koomneef et al. (1986. Transformation of tomato. In: Nevins D. J. and R. A. Jones, eds. Tomato Biotechnology. New York, N.Y., USA, Alan R. Liss, Inc. pp 169-178.). Plants were transformed and regenerated under kanamycin selection and primary regenerants ($T_0$) were grown to seed.

Expression Analysis of Transformants

Quantitative and qualitative β-glucuronidase (GUS) activity analyses were performed on $T_0$ plants.

Qualitative analysis of promoter activity was carried out using histological GUS assays.

Various plant parts were incubated overnight at 37° C. in the presence of atmospheric oxygen with Xgluc (5-Bromo-4-chloro-3-indolyl β-D-glucuronide cyclohexylamine salt) substrate in phosphate buffer (1 mg/ml, $K_2HPO_4$, 40 mM, $KH_2PO_4$, 10 mM, pH 7.2, 0.2% Triton X-100). The samples were de-stained by repeated washing with ethanol. Non-transgenic plants were used as negative controls. Trichomes of transgenic plants with ShzFPSp:GUS and ShTPS9p:GUS showed bright blue trichomes whereas the non-trichome tissues of these transgenic plants and the trichomes of non-transgenic control plants were unstained (FIGS. 1 and 2).

Quantitative analysis of promoter activity in trichomes of transgenic tomato plants was carried out using Q-PCR to determine the expression of GUS compared to that of a well-known trichome specific gene, namely *S. lycopersicum*

MKS1 (Uniprot E0YCS4_SOLLC; Sol Genomics Network entry Solyc01g108780.2). In order to isolate trichomes, leaf petioles and 4 cm pieces of stem were cut from transgenic and non-transgenic *S. lycopersicum* plants and immediately frozen in liquid nitrogen. Trichomes were collected from the frozen stem pieces by vortexing and were kept in liquid nitrogen or stored at −80° C. until further analyses. Three independent biological replicates were taken for each sample. Subsequently, total RNA was isolated with the Qiagen RNeasy® Plant Mini Kit according to the manufacturer's instructions. In brief, 50 mg of trichomes were ground in liquid nitrogen and the fine powder transferred to pre-frozen eppendorf tubes. The trichomes were disrupted, the cell lysate cleared from large debris and the total RNA bound to a column, purified and eluted. The supplied buffers were used in the described volumes. An average yield of 250 ng/µl total RNA was achieved. cDNA synthesis: Total RNA was first treated with the Promega RQ1 RNase-Free DNase kit to eliminate any remaining genomic DNA according to the manufacturer. Subsequently from 500 ng total RNA single stranded cDNA was synthesized primed by an anchored oligodT primer utilizing the Invitrogen Superscript™ II Reverse transcriptase kit. The cDNA was diluted threefold prior to further reactions.

In order to determine and compare the activity of the ShzFPS and ShTPS9 promoters (SEQ ID NO: 1 and 4, respectively) to the activity of a well-known trichome specific promoter in tomato (MKS1), we performed a qPCR analysis. The Roche Applied Science LightCycler® 480 DNA SYBR Green I Master kit was used for qPCR amplification of single stranded cDNA. Reactions were composed essentially following the manufacturer's protocol with 2 µl cDNA as input materials in a final volume of 15 µl. Reactions were performed in triple. Primers (as listed in Table 2) were used in a final concentration of 0.5 pmol/µl and were prior tested for linear and single product amplification characteristics. A LightCycler® 480 apparatus was utilized for the amplification reactions. The amplification profile was: 5 min 95° C.; 10 s 95° C., 20 s 58° C., 30 s 72° C.; 32 cycles. SYBR Green fluorescence signals were scored and Cp values were calculated by the LightCycler® 480 software. Automatic setting for background correction and cut-off were used. The delta delta Ct method was used to calculate concentration independent average promoter activities as compared to the expression of the endogenous *S. lycopersicum* MKS1 gene (known trichome-specific gene).

Figure 3:
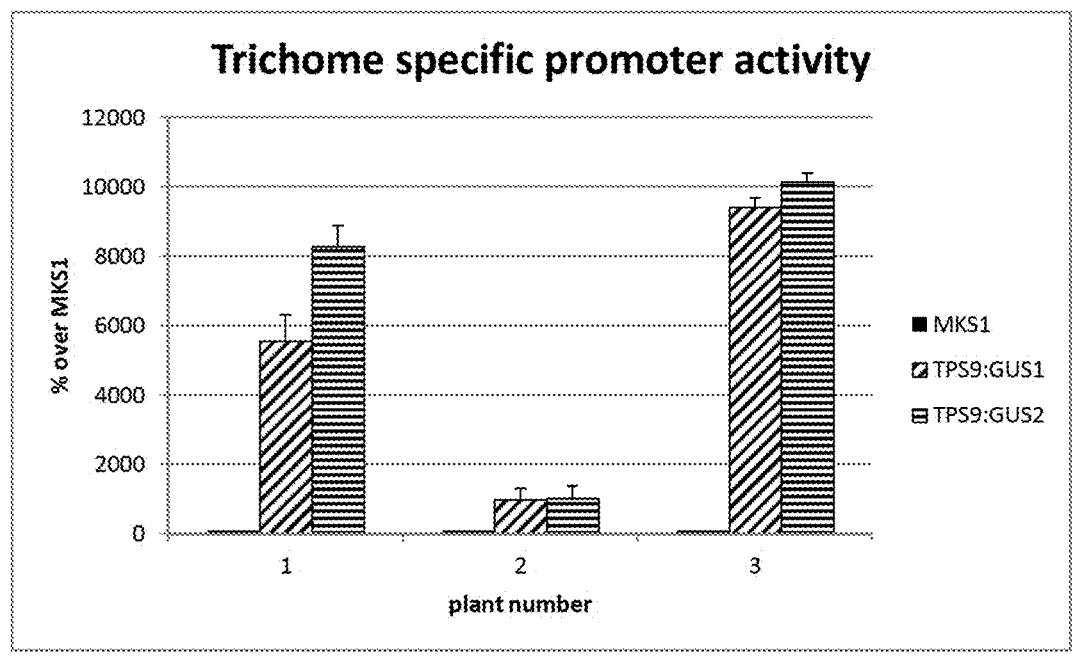
FIG. 3 shows trichome-specific expression of GUS. Q-PCR was performed with two independent sets of primers to determine the expression of GUS in trichomes of 3 independent transgenic plants transformed with GUS driven by the ShTPS9 promoter (SEQ ID NO: 4). The expression of an endogenous trichome-specific tomato gene, MKS1, was set to 100%. Evidently, the activity of the ShTPS9 promoter far exceeded (10-100 times) the activity of the SlMKS1 promoter.
Figure 4:
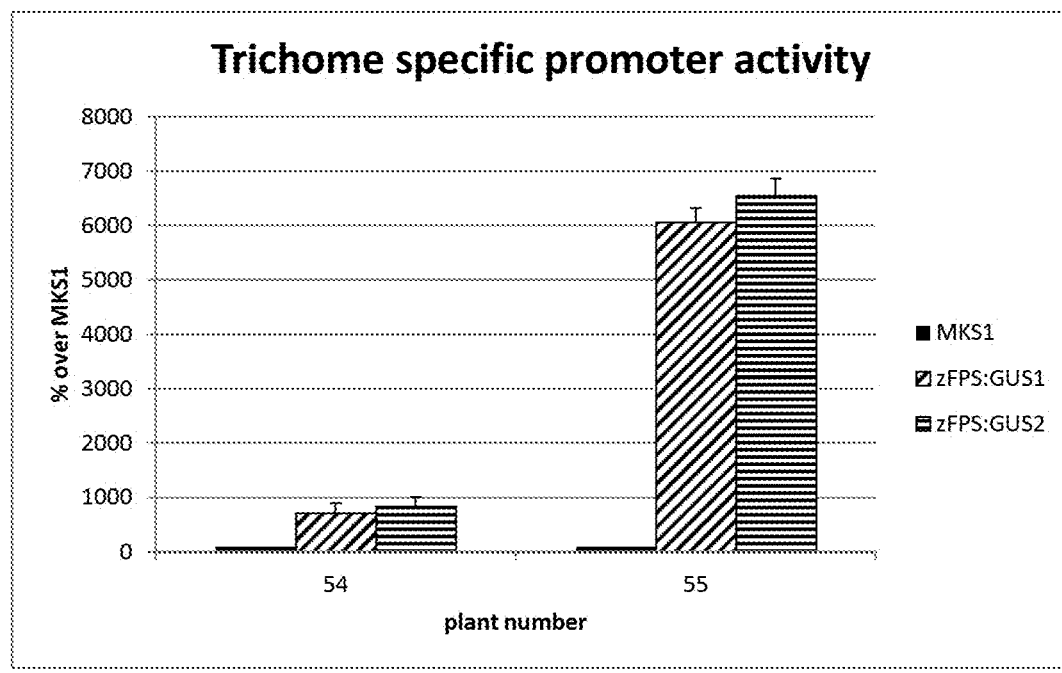
FIG. 4 shows trichome-specific expression of GUS. Q-PCR was performed with two independent sets of primers to determine the expression of GUS in trichomes of 2 independent transgenic plants transformed with GUS driven by the zFPS promoter (SEQ ID NO: 1). The expression of an endogenous trichome-specific *Solanum lycopersicum* gene, MKS1, was set to 100%. Evidently, the activity of the ShzFPS promoter far exceeded (8-65 times) the activity of the SlMKS1 promoter.

The qPCR data of several independent transformed tomato plants (expressing pShTPS9:GUS or pShzFPS:GUS) indicated that high levels of mRNA for GUS can be found in trichomes, indicating that the promoters of our invention are highly active and trichome-specific (FIGS. 3 and 4). Moreover, the promoter activity was orders of magnitude higher than that of a previously described tomato trichome-specific promoter MKS1 described in literature by Fridman et al. (2005; supra), Ben-Israel et al. (Plant Physiol. 2009, vol. 151(4):1952-1964) and Yu et al. (Plant Physiol. 2010, vol. 154(1): 67-77.) (FIGS. 3 and 4). In addition, it was clearly shown that the ShTPS9 and ShzFPS promoters have trichome-specific activity in plant species other than the species from which they were originally identified/isolated, namely *S. habrochaites*. This indicates that these promoters are, in addition to being highly active, of general use in trichomes of other plant species.

TABLE 2

| qPCR Primer sequences: | |
|---|---|
| MKS1: forward | 5' CCAAATATCGATGCAACCACC (SEQ ID NO: 27) |
| MKS1: reverse | 5' AAATCCTCAATTGGGCTCAG (SEQ ID NO: 28) |
| GUS1: forward | 5' CTGATAGCGCGTGACAAAAA (SEQ ID NO: 29) |
| GUS1: reverse | 5' GGCACAGCACATCAAAGAGA (SEQ ID NO: 30) |
| GUS2: forward | 5' CCCTTACGCTGAAGAGATGC (SEQ ID NO: 31) |
| GUS2: reverse | 5' TTTTTGTCACGCGCTATCAG (SEQ ID NO: 32) |

Transformation and Trichome-Specific Expression of ShZIS

A ShZIS promoter sequence (SEQ ID NO: 2) is placed in front of the GUS-A marker gene in the pKG1662 vector. Promoter and marker gene are subsequently shuttled into the multiple cloning site of the binary pBIN-plus vector (Van Engelen et al., 1995, Transgenic Res, 288). This construct is incorporated into *Agrobacterium tumefaciens* GV3101 and used to transform tomato *S. lycopersicum* var. Moneymaker, according to the method described by Koornneef et al. (1986. Transformation of tomato. In: Nevins D. J. and R. A. Jones, eds. Tomato Biotechnology. New York, N.Y., USA, Alan R. Liss, Inc. pp 169-178.). Plants are transformed and regenerated under kanamycin selection and primary regenerants ($T_0$) are grown to seed. GUS-expression analysis is performed and shows highly specific trichome expression in *S. lycopersicum*. Expression of GUS, and thus the activity of the ShZIS promoter, is significantly higher than that of known trichome-specific promoters described in the literature (e.g. ShMKS1). Moreover, it shows that ShZIS promoter is active in trichomes of another plant species than that from which it was isolated.

Increased Metabolite Production Through Metabolic Engineering Using the Promoters of this Invention.

High activity of ShzPFS, ShZIS and ShTPS9 promoters is shown using metabolic pathway engineering. Tomato plants are transformed with the CDS of ShzFPS (nucleic acid sequence encoding the amino acid sequence of SEQ ID NO:5) and ShZIS (nucleic acid sequence encoding the amino acid sequence of SEQ ID NO:6) driven by two known promoters SIMTS1 and ShMKS1, respectively, (WO2009/082208 and Fridman et al., 2005, supra, respectively) and the promoters of SEQ ID NO: 1, SEQ ID NO:2, or SEQ ID NO:4. To assess promoter activity transcript levels of ShzFPS and ShZIS are determined using Q-PCR. Moreover, zingiberene, the metabolic end product produced by the activity of ShzFPS and ShZIS, is determined by GC-MS in these sets of transgenic plants. Both assays indicate that the activity of the ShzFPS, ShZIS and ShTPS9 promoters is stronger than that of previously described trichome-specific promoters.

The invention claimed is:

1. A transgenic plant, plant cell, plant tissue, or plant organ, comprising a chimeric gene integrated in its genome, the chimeric gene comprising a trichome-specific promoter operably linked to a nucleic acid sequence coding for protein or RNA, wherein the promoter comprises the nucleic acid sequence of SEQ ID NO:4 or a nucleic acid sequence having at least 99% sequence identity with SEQ ID NO: 4.

2. The transgenic plant, plant cell, plant tissue or plant organ according to claim 1, wherein the promoter is specifically active in glandular trichomes.

3. The transgenic plant, plant cell, plant tissue or plant organ according to claim 1, wherein the promoter has constitutive activity in trichomes.

4. The transgenic plant, plant cell, plant tissue or plant organ according to claim 1, wherein the promoter activity is not significantly reduced when the plant, plant cell, plant tissue or plant organ is exposed to one or more biotic and/or abiotic stresses.

5. The transgenic plant, plant cell, plant tissue or plant organ according to claim 1, wherein the plant belongs to the family Solanaceae.

6. A chimeric gene comprising a first nucleic acid sequence having trichome-specific promoter activity when introduced into plant cells, operably linked to a second nucleic acid sequence coding for protein or RNA, wherein the first nucleic acid and the second nucleic acid are not operably linked to each other in nature, and wherein the first nucleic acid sequence comprises SEQ ID NO:4 or has at least 99% sequence identity with SEQ ID NO: 4 or SEQ ID NO: 3.

7. The chimeric gene according to claim 6, wherein the first and second nucleic acid sequences are operably linked to a 3' UTR sequence.

8. A vector comprising the chimeric gene according to claim 6.

9. A transgenic plant or plant cell comprising the vector according to claim 8.

10. A method for making a transgenic plant or plant cell, comprising:
(a) generating a vector according to claim 8;
(b) transforming a plant or plant cell with the vector; and, optionally,
(c) regenerating transgenic plants.

11. A transgenic plant or plant cell obtainable or obtained by the method of claim 10.

12. The transgenic plant or plant cell according to claim 11, which is a *Solanum lycopersicum* plant or plant cell.

13. The transgenic plant, plant cell, plant tissue, or plant organ according to claim 1, wherein the nucleic acid sequence coding for protein or RNA is further operably linked to a 3′ UTR sequence.

\* \* \* \* \*

SEQUENCE LISTING

<160> NUMBER OF SEQ ID NOS: 32

<210> SEQ ID NO 1
<211> LENGTH: 2254
<212> TYPE: DNA
<213> ORGANISM: Solanum habrochaites

<400> SEQUENCE: 1

```
tggccattac gtggactaat ttttttacaa taaatgatca ctttattttt aacaagtatg      60
attaataatt aattgaaatt agtgagtttg aaatttgact tttgtttagc ctatgagcaa     120
acctttaaag ttaattcaaa attaaaagtt attgattttt aatcatgttt atgaatcaaa     180
tgtgatcaaa aggtcaaaat caactgtctc ccaaataatt tttttaaact cgagatgatt     240
tgaaattttt ttcaaccaat agttatattt tccaatgtca tattattaaa aacttgaggc     300
taattccatc ctggaattta tgactatagt tatagttatc ttagactctt agctgcgtta     360
tagtcagact tgataattat taaaaagtgt gtgactctga tttttcacat atgacgattt     420
gagaaattga taatctagaa agctatatca tgaaaaattc taagaatgat tgaagataat     480
aagaatattt tgaaatatcg caaccctacc acaaagtttt accaacctat tttcttttat     540
atagatatga gctatatgac acatggaaat acaattataa agcagtagtt agaggtgaat     600
taatattgaa ttttaaaggg aataatcaat ggatgatatc tttttttactt tttttctttt     660 tatcactaaa agtgcattca ttgtagacta aaacacatta aatagagttt tatatccttt     720
tctcatacat ggtccctcat tttcttctta gtcttgtatt ataagtcacc tcttttaaa     780 aataattgga tcataatata tgttatttta taaaatttat gcataaaata tcatattttg     840
ctcattatat ttttattgat taattaataa tcttaaaata tatttatttt gactgatctt     900
gaaaatcaat aactaattaa ataagggcat agaaataaaa ttatcttatt tcttgttaca     960
agtacaaata caaaaagtga cttataatat gggacggggg gagtaattaa gtgaaaggtt    1020
attcgttctt tattggtatt atcagttatt taggagataa ctgatttagc aattttttagt   1080 ctttatttat tttatacaca gtttataaaa catacttaca tttttgaact tggtgatggc    1140
gtagcccagg ggtgttaaat gggcgggttg ggttgaaatt ggaaatatta ctatgggtga    1200
atagaaattg ggttgggttt gacccgccca aatttactttt gggctcaaat gagctaaaat   1260
atgggttggg tcttgacccg ctcaatttga cccgcttaat cttagttatt taacatattg    1320
atatttaatt tttataatca caatttgaat ctccgttcaa gaattttttt tttataataa    1380
aagtaacaaa tggatagata aatcataaaa aaaaagcaac aaatcgataa taattcatac    1440
tgtaaatata ggaacatatc ttaatactaa gttataaaac aggttgaaat tagtaattga    1500
attgggctca attgagaatt ctcttcaaat aggttaagct tgaatgggtt gaggttgaac    1560
ccaactcaaa ttatcttgag ctcaatcctt aaaattctga gcgtattggg catgttacca    1620
tgtttgggtt catttttaac gccctagcg tagtcgaaag aagtcaatcc atgaggtttg     1680
taaaacaaat gcgaataatt tactctacca ttgagcttgt tagtcatatg gtgtagcaaa    1740
atggtagatt atcgaaaaaa tatcttaatt atgcttcata gttataattt gttaattaca    1800
attagtagct acatgttata tggaggagag tggcgagcga gattgggaga ggaaagagag    1860
aagtgagtga gacaaggtag agagtgggag agaggcgaac tgcatatgca tatttgtcaa    1920 ataattgta tatatgtaac tggtatacat acgtattcgt atatctggtg agtgaggaga    1980 gaaagagag aagcgagcga gattggaaga ggaaagagag agccgagcga gagaggacaa     2040
taatttatgt aattcgcatc tcatttgtat aattaatttt gttcgaaatg cggttcaata    2100
```

```
taattttttta accataagca taaacaaccc tatatagaac tattgatcaa tatagaacta      2160
ttgatctatt gatcaaaaga gtcataccat aattctattt aaacaccacc tcccttgttt      2220
cacttcacaa taaataaat ttgagtaata aagc                                   2254
```

<210> SEQ ID NO 2
<211> LENGTH: 3451
<212> TYPE: DNA
<213> ORGANISM: Solanum habrochaites

<400> SEQUENCE: 2

```
ctctctctaa agaagttgaa gataccttct tccagtaagt gggactggag ggggagattt        60
gttgaatcca tcccattttt tttggtcaac tttagctact caattggtac aagcaattgt       120
taaaaaggaa tagtaattgg agttgaaaag aaaagatttg gtagttggca aattggtaag       180
atttgcaacc atttttgact ttgctatgtt tacatatgtc attagtgaca taggtatggt       240
tttatccttc tataaatagc gcactcttgc tcatttgtag aacacaccaa gttagagaga       300
aaacaatttt tgagagcaaa gtgaggtatt ccatagacta tataagaaaa tagtctgtga       360
agaaaaatag agtgtgagcg atattttagt aagacggaaa ccaaaagagt gttgttcctt       420
ttgagtgtgt agtagtcact ttgagtattg tattcgtgac tacacagtgt aaaattcctt       480
actatagtaa tatcaattgc tcctcttagt ccgcggtttt ttcccttatt cagaagggtt       540
tccacgtaaa attcttggtg tcattatttt cccattttat ttccattact tttaccatat       600 atactttgt gcttgtccgc gttttcccaa caagatggtg tttaaataga attatggtat        660
gactcttttg atcaatagtt ctatataggg ttgttcatgc ttatggttaa aaaatcatat       720
tgaatcgcat ttcgaatcaa aattgataat acaaatgaga tgcgaagctt gcatgagttc       780
caaaaaatat aaataacggt aaaatggtaa agttacatca ttttttaatg caactgcaaa       840
gtaaaaatat aacatataaa atgagacaga ggaagtatgt aaaatcaata atgaatatgt       900
attactccct ctatttcata ataacttaag ctttgaagtg tttcacaccc tttaaaaaaa       960
gtaggttagg acataaatga acataatttt tcattttgt ccttattaat tattgtcaaa       1020
aataactaaa cattaattat aataactaat tccaatacta acttaatggg taaaattaga      1080
agaaattttt taaaatagtc ttgaaaattt aaaacataag ttaattgaaa atggaaaga       1140 aaaaaagct caaatcttgt tattatgtaa tggagggagt attagacaga gaaattatta      1200
attrctccct ccgtcccata ttataagtca ctttttttcat ttgtacttgc aacaagaaat      1260
aagataattt tattctctatg cccttttgtta tagattttca aaattagtca aagtaaatat      1320 atttttcaaaa ytaattaatt aatcaataag gatataatga gcaaaatatg gtatttagta      1380
taaatttata aatacatata ttatgatcaa tatttagaga aggtgaccta taatatgaag      1440
gaagaaatga ggaccatata tgagaaagga tataaactct atttaatgtg tttagtgtac      1500
aatgaatgca ctttagtgat aaagaaaaaa gttaaaaaaa tatcatccat gattattccc      1560
tttaaaattc gatattagtt caccctctaac tacttacaat aattgtattt ccatgtgtca      1620
tatagctcat atttatataa agaaaatagg ttggtaaaac tttgtggtag gtttgagata      1680
tttcaaaata ttcttataat ttttcaatta ttcttccaat tttttcatga tatagctttc      1740
tagatcatca atttttcttaa atcgtcatat gtgaaaattg gagtcacaca cttttttaata      1800 gttatcaagt ttgactatag cgcagctaag agtctaagat aactataaca ataatcataa      1860
attacaggat ggaattagcc tcaagtttgt aataacatga cattcgaaaa tataaccatt      1920
```

```
ggataaaaaa aatttcaaat catctcgagt ttataaaaat tatttgagag acagttgatt    1980
ttgacctttt gatcacgtgt gattcataaa catgatcaaa aatcaacaat ttttaatttt    2040
taattgactt taaaggtttg ctaataggct aaacggaagt caaatttcaa actcactatt    2100
tcaattaatt attaatcata ctatgttaaa aatagtccac gtaatggcca caactagca    2160 aaacttatca cgagattcta tatgatacta tatatgcttt gttttttcga tattcatttt    2220
atttaaagtt tgatatttat attaaaatta aaatagattt taaatttgta ttaagaaaat    2280
tcattataaa aggttgaaac attttctaac aaaagatat gatgtccact tgaatcaaag    2340
agtaataatg ctcatatact ttttctgctt tgaaataaga tatgcgataa tgattgacta    2400
ataaaaatta aagactagtc atttataggg caaaacgtgc attttacat ttaattacac    2460 atcaagktta taccaaagtg agatattata aggaaaaatc tttgtggcca aaattttgg    2520 acagaacgat attttattta tgttatttta atttttaatac attttaacta caaaatggaa    2580
aaaataacag tttattataa aataaaaaaa tattttagtt ttttttatt ttttagtcaa    2640 tttttctagc catttagctc tttccatatt ataatataaa gagaaagta tttaaaatat    2700 ctctaaattt ggtgtgaatt aataggtttg tctccgaatt attgacaaca ttaaaactac    2760
tctctacttg acaaattgaa cttaaacata tatacccttg atcttgtcac atcagtgata    2820
tacaatccca aattctcgtc aactttaggg gtattttgaa cacttctttt gacattttat    2880
taagagtctc acgttcctac aagagtttga gactacttga tatgccatgt ggcagactgg    2940
agtgtatttt aagttcagtt agtcaactaa acaattttttt tagagtaaat tttaggttta    3000
acaaacataa aaatcatata tgtatgttaa taattatagt tggtataatt gcgcttcata    3060
gcaaacttta tgtttgctat gactattaat ttgtatattt tgatatacat atacaaaaga    3120
atgaattgta taatctctat ttgtataaag cgagaacgag agaagacaaa tgaaaactgg    3180
tagcgagaaa tggagagtga cgaaagacaa ctgtttaatt tgaatcaatg atttgctatt    3240
ttatacattt tttccttatt tttaagacta tcaataattg agtgacgaaa ttaataattt    3300
gcattaaatt taattaaaaa tattttcaac atttctctcc gctaaatatt tatttataac    3360
gaggaaacaa aatcaaagac aaacacaaaa taggagaaat tcttcatttt ttgacccctc    3420
cactcccaaa aacaacacac aatattcaag g                                  3451
```

<210> SEQ ID NO 3
<211> LENGTH: 530
<212> TYPE: DNA
<213> ORGANISM: Solanum habrochaites

<400> SEQUENCE: 3

```
ttatttcact aattaaattt attcttaaat atttatatat atttattttg ctatgctaat      60 ttatttttt tataataaaa ttagttgagt gatttgatgg atacaaagtc ataaattgaa     120
tgacttaact aaataaatta ttaaagttga atgatattat tgataaaaag acataaattg     180
aataattttt ttgatataaa ataaagttca gatattgtta cacaattaac catccttttc     240
aattttaata ataaactcc tctttaatat cgttctaatg aaaatttctt ccaaacaaca     300
taaataataa gttcatcatt tatcgactaa ttcataaata ttatttgagt aatatctatg     360
caatttttta caatgtttat attatgtcat ttaaaagata aggacagatg ccggtaagca     420
ttacaataag tggtagtaac tacattataa ataggcccat ccaattagca taacttaaac     480
ccacaaatta agcttgaaaa aaaaagagca aaccttagaa caaacaagca                530
```

<210> SEQ ID NO 4
<211> LENGTH: 1875
<212> TYPE: DNA
<213> ORGANISM: Solanum habrochaites

<400> SEQUENCE: 4

| | | | | | |
|---|---|---|---|---|---|
| tttaaattt | atatttatat | taaacatttt | attaatatat | atatatatat | agctataaac | 60 |
| tcaataatta | cgatgactta | ctataaattc | gattttaagt | ttgaactcaa | aaattcttaa | 120 |
| aactctaatt | ctacttgtgt | attcatctag | cctcttatga | cacgtaaaaa | aaaatacaat | 180 |
| aaataaattg | caataactca | aattatttat | atgtgacata | agaatcgtg | tggctctaaa | 240 |
| attttatttc | tctgcggtcc | aattaaagtt | ttgataatcc | accaaattga | agacttaaaa | 300 |
| tgccttattg | aggtgccaaa | tactaatgaa | gaagaaaaca | aacaaaata | aaaacaccta | 360 |
| ctcataaatt | ataatataac | tgtatctcat | tgctaatatg | acatttaata | ggagagtatg | 420 |
| aaaatcgata | attaggatat | attgttaata | tataatcaaa | cgttttattt | cttcctagtg | 480 |
| gtagagtaag | gttctaatct | agagccccta | tccccttacc | attactgttt | agtattatgc | 540 |
| aagttatttt | tttactttga | ttatctctaa | tatttttact | gtcgttattt | ttgttttttt | 600 |
| aatataattt | ttgtcatatt | ttttgctgtt | acaatacttt | caaatcatgt | tttgaagaat | 660 |
| gatttcttga | tccgaggatc | tatagtaaac | attctttcta | tcaaataaag | atacatataa | 720 |
| cttataaggt | ctgcatacat | aatactatcc | ttctcaaacc | ccacttatat | gaaatgatac | 780 |
| cagatgactg | agtcaatatc | tcaaaaggtc | actcaagttt | aagaatatat | ctagtaaagt | 840 |
| tattaaactt | tctttactat | caataaaatc | acttaactta | gatacgtgga | tcaataaaat | 900 |
| cactcaactc | aatttatcat | taaaaaaatt | atcatagata | aataattttt | tatgccatgt | 960 |
| aaatatgaac | tccataaatt | aataaaatta | aaaaaaatcc | atcaagactt | ttttatgaat | 1020 |
| aaacttaata | atttattagg | atattattat | ataattctaa | tgtattatta | cgagctttat | 1080 |
| taagaaaaag | ttagggtatt | gtatggtaaa | taattggggg | tacatgattt | ttatcatata | 1140 |
| aaaatatata | gacattggct | taataactct | aactctgcaa | atattactct | gttacgatca | 1200 |
| ttaaattata | aaaataaatt | gacgtcttat | aattattttt | cgttgcaatc | attaagccct | 1260 |
| atgacaatat | cagtatatag | taattggtaa | tgtaacattc | attctgatac | caattttaag | 1320 |
| tgcataataa | tattatatta | atatttattt | cactaattaa | atttattctt | aaatatttat | 1380 |
| atatatttat | tttgctatgc | taatttatttt | ttttataat | aaaattagtt | gagtgatttg | 1440 |
| atggatacaa | agtcataaat | tgaatgactt | aactaaataa | attattaaag | ttgaatgata | 1500 |
| ttattgataa | aaagacataa | attgaataat | tttttgata | taaaataaag | ttcagatatt | 1560 |
| gttacacaat | taaccatcct | tttcaatttt | aataaataaa | ctcctctta | atatcgttct | 1620 |
| aatgaaaatt | tcttccaaac | aacataaata | ataagttcat | catttatcga | ctaattcata | 1680 |
| aatattattt | gagtaatatc | tatgcaattt | tttacaatgt | ttatattatg | tcatttaaaa | 1740 |
| gataaggaca | gatgccggta | agcattacaa | taagtggtag | taactacatt | ataaataggc | 1800 |
| ccatccaatt | agcataactt | aaacccacaa | attaagcttg | aaaaaaaaaa | gagcaaacct | 1860 |
| tagaacaaac | aagca | | | | | 1875 |

<210> SEQ ID NO 5
<211> LENGTH: 258
<212> TYPE: PRT
<213> ORGANISM: Solanum habrochaites

<400> SEQUENCE: 5

```
Ala Arg Gly Leu Asn Lys Ile Ser Cys Ser Leu Ser Leu Gln Thr Glu
1               5                   10                  15

Lys Leu Cys Tyr Glu Asp Asn Asp Asn Leu Asp Glu Glu Leu Met
            20                  25                  30

Pro Lys His Ile Ala Leu Ile Met Asp Gly Asn Arg Arg Trp Ala Lys
            35                  40                  45

Asp Lys Gly Leu Asp Val Ser Glu Gly His Lys His Leu Phe Pro Lys
50                  55                  60

Leu Lys Glu Ile Cys Asp Ile Ser Ser Lys Leu Gly Ile Gln Val Ile
65                  70                  75                  80

Thr Ala Phe Ala Phe Ser Thr Glu Asn Trp Lys Arg Ala Lys Gly Glu
                85                  90                  95

Val Asp Phe Leu Met Gln Met Phe Glu Glu Leu Tyr Asp Glu Phe Ser
            100                 105                 110

Arg Ser Gly Val Arg Val Ser Ile Ile Gly Cys Lys Thr Asp Leu Pro
            115                 120                 125

Met Thr Leu Gln Lys Cys Ile Ala Leu Thr Glu Glu Thr Thr Lys Gly
            130                 135                 140

Asn Lys Gly Leu His Leu Val Ile Ala Leu Asn Tyr Gly Gly Tyr Tyr
145                 150                 155                 160

Asp Ile Leu Gln Ala Thr Lys Ser Ile Val Asn Lys Ala Met Asn Gly
            165                 170                 175

Leu Leu Asp Val Glu Asn Ile Asn Lys Asn Leu Phe Asp Gln Glu Leu
            180                 185                 190

Glu Ser Lys Cys Pro Asn Pro Asp Leu Leu Ile Arg Thr Gly Gly Val
            195                 200                 205

Gln Arg Val Ser Asn Phe Leu Leu Trp Gln Leu Ala Tyr Thr Glu Phe
            210                 215                 220

Tyr Phe Thr Lys Thr Leu Phe Pro Asp Phe Gly Glu Glu Asp Leu Lys
225                 230                 235                 240

Glu Ala Ile Ile Asn Phe Gln Gln Arg His Arg Phe Gly Gly His
            245                 250                 255

Thr Tyr

<210> SEQ ID NO 6
<211> LENGTH: 741
<212> TYPE: PRT
<213> ORGANISM: Solanum habrochaites

<400> SEQUENCE: 6

Cys Ser His Ser Thr Pro Ser Ser Met Asn Gly Phe Glu Asp Ala Arg
1               5                   10                  15

Asp Arg Ile Arg Glu Ser Phe Gly Lys Val Glu Leu Ser Pro Ser Ser
            20                  25                  30

Tyr Asp Thr Ala Trp Val Ala Met Val Pro Ser Lys His Ser Leu Asn
            35                  40                  45

Glu Pro Cys Phe Pro Gln Cys Leu Asp Trp Ile Ile Glu Asn Gln Arg
50                  55                  60

Glu Asp Gly Ser Trp Gly Leu Asn Pro Ser His Pro Leu Leu Leu Lys
65                  70                  75                  80

Asp Ser Leu Ser Ser Thr Leu Ala Cys Leu Leu Ala Leu Thr Lys Trp
                85                  90                  95

Arg Val Gly Asp Glu Gln Ile Lys Arg Gly Leu Gly Phe Ile Glu Thr
            100                 105                 110
```

-continued

Gln Ser Trp Ala Ile Asp Asn Lys Asp Gln Ile Ser Pro Leu Gly Phe
        115                 120                 125

Glu Ile Ile Phe Pro Ser Met Ile Lys Ser Ala Glu Lys Leu Asn Leu
130                 135                 140

Asn Leu Ala Ile Asn Lys Arg Asp Ser Thr Ile Lys Arg Ala Leu Gln
145                 150                 155                 160

Asn Glu Phe Thr Arg Asn Ile Glu Tyr Met Ser Gly Phe Gly Glu
                165                 170                 175

Leu Cys Asp Trp Lys Glu Ile Ile Lys Leu His Gln Arg Gln Asn Gly
            180                 185                 190

Ser Leu Phe Asp Ser Pro Ala Thr Thr Ala Ala Leu Ile Tyr His
                195                 200                 205

Gln His Asp Lys Lys Cys Tyr Glu Tyr Leu Asn Ser Ile Leu Gln Gln
        210                 215                 220

His Lys Asn Trp Val Pro Thr Met Tyr Pro Thr Lys Ile His Ser Leu
225                 230                 235                 240

Leu Cys Leu Val Asp Thr Leu Gln Asn Leu Gly Val His Arg His Phe
                245                 250                 255

Lys Ser Glu Ile Lys Lys Ala Leu Asp Glu Ile Tyr Arg Leu Trp Gln
            260                 265                 270

Gln Lys Asn Glu Glu Ile Phe Ser Asn Val Thr His Cys Ala Met Ala
        275                 280                 285

Phe Arg Leu Leu Arg Ile Ser Tyr Tyr Asp Val Ser Ser Asp Glu Leu
        290                 295                 300

Ala Glu Phe Val Asp Glu His Phe Phe Ala Thr Ser Gly Lys Tyr
305                 310                 315                 320

Thr Ser His Val Glu Ile Leu Glu Leu His Lys Ala Ser Gln Leu Ala
                325                 330                 335

Ile Asp His Glu Lys Asp Ile Leu Asp Lys Ile Asn Asn Trp Thr
            340                 345                 350

Arg Thr Phe Met Glu Gln Lys Leu Leu Asn Asn Gly Phe Ile Asp Arg
        355                 360                 365

Met Ser Lys Lys Glu Val Glu Leu Ala Leu Arg Asn Phe Tyr Ile Ile
370                 375                 380

Ser Asp Leu Ala Glu Asn Arg Arg Tyr Ile Lys Ser Tyr Glu Glu Asn
385                 390                 395                 400

Asn Phe Lys Ile Leu Lys Ala Ala Tyr Arg Ser Pro Asn Ile Asn Asn
                405                 410                 415

Lys Asp Leu Phe Ile Phe Ser Ile Arg Asp Phe Glu Leu Cys Gln Ala
            420                 425                 430

Gln His Gln Glu Glu Leu Gln Gln Leu Lys Arg Trp Phe Glu Asp Cys
        435                 440                 445

Arg Leu Asp Gln Leu Gly Leu Ser Glu Gln Phe Ile Ser Ala Ser Tyr
450                 455                 460

Leu Cys Ala Ile Pro Ile Val Pro Gly Pro Glu Leu Ser Asp Ala Arg
465                 470                 475                 480

Leu Val Tyr Ala Lys Tyr Val Met Leu Leu Thr Ile Val Asp Asp His
                485                 490                 495

Phe Glu Ser Phe Ala Ser Thr Asp Glu Cys Leu Asn Ile Ile Glu Leu
            500                 505                 510

Val Glu Arg Trp Asp Asp Tyr Ala Ser Val Gly Tyr Lys Ser Glu Arg
        515                 520                 525

Val Lys Val Leu Phe Ser Met Phe Tyr Lys Ser Ile Glu Glu Ile Ala

```
            530                 535                 540
Thr Ile Ala Glu Ile Lys Gln Gly Arg Ser Val Lys Asn His Leu Ile
545                 550                 555                 560

Asn Leu Trp Leu Lys Val Met Lys Leu Met Leu Met Glu Arg Val Glu
                565                 570                 575

Trp Cys Ser Gly Lys Thr Ile Pro Arg Ile Glu Glu Tyr Leu Tyr Val
                580                 585                 590

Ser Ser Ile Thr Phe Gly Ser Arg Leu Ile Pro Leu Thr Thr Gln Tyr
                595                 600                 605

Phe Ile Gly Ile Lys Ile Ser Lys Asp Leu Leu Glu Ser Asp Glu Ile
                610                 615                 620

Tyr Gly Leu Cys Asn Phe Thr Gly Ile Val Leu Arg Leu Leu Asn Asp
625                 630                 635                 640

Leu Gln Asp Ser Lys Arg Glu Gln Lys Glu Gly Ser Ile Asn Leu Val
                645                 650                 655

Thr Leu Leu Met Lys Ser Ile Ser Glu Glu Ala Ile Met Lys Met
                660                 665                 670

Lys Glu Ile Leu Glu Met Lys Arg Arg Glu Leu Phe Lys Met Val Leu
                675                 680                 685

Val Gln Lys Lys Gly Ser Gln Leu Pro Gln Leu Cys Lys Glu Ile Phe
                690                 695                 700

Trp Arg Thr Cys Lys Trp Ala His Phe Thr Tyr Ser Gln Thr Asp Arg
705                 710                 715                 720

Tyr Arg Phe Pro Glu Glu Met Glu Asn His Ile Asp Glu Val Phe Tyr
                725                 730                 735

Lys Pro Leu Asn His
                740

<210> SEQ ID NO 7
<211> LENGTH: 45
<212> TYPE: PRT
<213> ORGANISM: Solanum habrochaites

<400> SEQUENCE: 7

Met Ser Ser Leu Val Leu Gln Cys Trp Lys Leu Ser Ser Pro Ser Leu
1               5                   10                  15

Ile Leu Gln Gln Asn Thr Ser Ile Ser Met Gly Ala Phe Lys Gly Ile
                20                  25                  30

His Lys Leu Gln Ile Pro Asn Ser Pro Leu Thr Val Ser
                35                  40                  45

<210> SEQ ID NO 8
<211> LENGTH: 36
<212> TYPE: PRT
<213> ORGANISM: Solanum habrochaites

<400> SEQUENCE: 8

Met Ile Val Gly Tyr Arg Ser Thr Ile Ile Thr Leu Ser His Pro Lys
1               5                   10                  15

Leu Gly Asn Gly Lys Thr Ile Ser Ser Asn Ala Ile Phe Arg Arg Ser
                20                  25                  30

Cys Arg Val Arg
                35

<210> SEQ ID NO 9
<211> LENGTH: 22
<212> TYPE: DNA
```

<213> ORGANISM: Artificial sequence
<220> FEATURE:
<223> OTHER INFORMATION: Adapter Primer1

<400> SEQUENCE: 9
gtaatacgac tcactatagg gc                                        22

<210> SEQ ID NO 10
<211> LENGTH: 19
<212> TYPE: DNA
<213> ORGANISM: Artificial sequence
<220> FEATURE:
<223> OTHER INFORMATION: Nested Adaptor Primer 2

<400> SEQUENCE: 10
actatagggc acgcgtggt                                            19

<210> SEQ ID NO 11
<211> LENGTH: 32
<212> TYPE: DNA
<213> ORGANISM: Artificial sequence
<220> FEATURE:
<223> OTHER INFORMATION: Primer Intron 1 of ShzFPS

<400> SEQUENCE: 11
gtgtacgtat ataaggtatg aacaaaaact ac                             32

<210> SEQ ID NO 12
<211> LENGTH: 31
<212> TYPE: DNA
<213> ORGANISM: Artificial sequence
<220> FEATURE:
<223> OTHER INFORMATION: Nested Primer Round 1 ShzFPS

<400> SEQUENCE: 12
ctaaagtaat taattcccat aagtaattaa c                              31

<210> SEQ ID NO 13
<211> LENGTH: 30
<212> TYPE: DNA
<213> ORGANISM: Artificial sequence
<220> FEATURE:
<223> OTHER INFORMATION: Promoter Primer 1 Round 2 ShzFPS

<400> SEQUENCE: 13
gattgacttc tttcgactac gctaggggcg                                30

<210> SEQ ID NO 14
<211> LENGTH: 30
<212> TYPE: DNA
<213> ORGANISM: Artificial sequence
<220> FEATURE:
<223> OTHER INFORMATION: Nested primer Round 2 ShzFPS

<400> SEQUENCE: 14
cccaaacatg gtaacatgcc caatacgctc                                30

<210> SEQ ID NO 15
<211> LENGTH: 44
<212> TYPE: DNA
<213> ORGANISM: Artificial sequence
<220> FEATURE:
<223> OTHER INFORMATION: Promoter Primer 2 Round 3 ShzFPS

<400> SEQUENCE: 15
ctctatttaa tgtgttttag tctacaatga atgcactttt agtg                44

<210> SEQ ID NO 16
<211> LENGTH: 41
<212> TYPE: DNA
<213> ORGANISM: Artificial sequence
<220> FEATURE:
<223> OTHER INFORMATION: Nested primer Round 3 ShzFPS

<400> SEQUENCE: 16
caagactaag aagaaaatga gggaccatgt atgagaaaag g        41

<210> SEQ ID NO 17
<211> LENGTH: 23
<212> TYPE: DNA
<213> ORGANISM: Artificial sequence
<220> FEATURE:
<223> OTHER INFORMATION: Primer Exon 1 of ShZIS

<400> SEQUENCE: 17
cattgatgaa ggggtactgt ggc        23

<210> SEQ ID NO 18
<211> LENGTH: 23
<212> TYPE: DNA
<213> ORGANISM: Artificial sequence
<220> FEATURE:
<223> OTHER INFORMATION: Nested primer Round 1 ShZIS

<400> SEQUENCE: 18
tgcatcttac tctacatgat ctc        23

<210> SEQ ID NO 19
<211> LENGTH: 42
<212> TYPE: DNA
<213> ORGANISM: Artificial sequence
<220> FEATURE:
<223> OTHER INFORMATION: Promoter Primer 1 Round 2 ShZIS

<400> SEQUENCE: 19
cgagaatttg ggattgtata tcactgatgt gacaagatca ag        42

<210> SEQ ID NO 20
<211> LENGTH: 43
<212> TYPE: DNA
<213> ORGANISM: Artificial sequence
<220> FEATURE:
<223> OTHER INFORMATION: Nested primer Round 2 ShZIS

<400> SEQUENCE: 20
gtagagagta gttttaatgt tgtcaataat tcggagacaa acc        43

<210> SEQ ID NO 21
<211> LENGTH: 44
<212> TYPE: DNA
<213> ORGANISM: Artificial sequence
<220> FEATURE:
<223> OTHER INFORMATION: Promoter Primer 2 Round 3 ShZIS

<400> SEQUENCE: 21
caaagcatat atagtatcat atagaatctc gtgataagtt ttgc        44

<210> SEQ ID NO 22
<211> LENGTH: 37
<212> TYPE: DNA
<213> ORGANISM: Artificial sequence
<220> FEATURE:

<223> OTHER INFORMATION: Nested primer Round 3 ShZIS

<400> SEQUENCE: 22
gtgataagtt ttgctagttg ttggccatta cgtggac                                37

<210> SEQ ID NO 23
<211> LENGTH: 28
<212> TYPE: DNA
<213> ORGANISM: Artificial sequence
<220> FEATURE:
<223> OTHER INFORMATION: Primer Exon 1 of ShTPS9

<400> SEQUENCE: 23
cgtaaatgga tatgtatctc cttgcttc                                          28

<210> SEQ ID NO 24
<211> LENGTH: 27
<212> TYPE: DNA
<213> ORGANISM: Artificial sequence
<220> FEATURE:
<223> OTHER INFORMATION: Nested primer Round 1 ShTPS9

<400> SEQUENCE: 24
gcttcactaa cttcaacctt aagagag                                           27

<210> SEQ ID NO 25
<211> LENGTH: 48
<212> TYPE: DNA
<213> ORGANISM: Artificial sequence
<220> FEATURE:
<223> OTHER INFORMATION: Promoter primer 1 round 2 ShTPS9

<400> SEQUENCE: 25
gaaaaggatg gttaattgtg taacaatatc tgaactttat tttatatc                    48

<210> SEQ ID NO 26
<211> LENGTH: 46
<212> TYPE: DNA
<213> ORGANISM: Artificial sequence
<220> FEATURE:
<223> OTHER INFORMATION: Nested primer Round 2 ShTPS9

<400> SEQUENCE: 26
gttaagtcat tcaatttatg actttgtatc catcaaatca ctcaac                      46

<210> SEQ ID NO 27
<211> LENGTH: 21
<212> TYPE: DNA
<213> ORGANISM: Artificial sequence
<220> FEATURE:
<223> OTHER INFORMATION: MKS1 forward qPCR primer

<400> SEQUENCE: 27
ccaaatatcg atgcaaccac c                                                 21

<210> SEQ ID NO 28
<211> LENGTH: 20
<212> TYPE: DNA
<213> ORGANISM: Artificial sequence
<220> FEATURE:
<223> OTHER INFORMATION: MKS1 reverse qPCR primer

<400> SEQUENCE: 28
aaatcctcaa ttgggctcag                                                   20

```
<210> SEQ ID NO 29
<211> LENGTH: 20
<212> TYPE: DNA
<213> ORGANISM: Artificial sequence
<220> FEATURE:
<223> OTHER INFORMATION: GUS1 forward qPCR primer

<400> SEQUENCE: 29
ctgatagcgc gtgacaaaaa                                           20

<210> SEQ ID NO 30
<211> LENGTH: 20
<212> TYPE: DNA
<213> ORGANISM: Artificial sequence
<220> FEATURE:
<223> OTHER INFORMATION: GUS1 reverse qPCR primer

<400> SEQUENCE: 30
ggcacagcac atcaaagaga                                           20

<210> SEQ ID NO 31
<211> LENGTH: 20
<212> TYPE: DNA
<213> ORGANISM: Artificial sequence
<220> FEATURE:
<223> OTHER INFORMATION: GUS2 forward qPCR primer

<400> SEQUENCE: 31
cccttacgct gaagagatgc                                           20

<210> SEQ ID NO 32
<211> LENGTH: 20
<212> TYPE: DNA
<213> ORGANISM: Artificial sequence
<220> FEATURE:
<223> OTHER INFORMATION: GUS2 reverse qPCR primer

<400> SEQUENCE: 32
tttttgtcac gcgctatcag                                           20
```